US012758489B2

(12) United States Patent
Cho et al.

(10) Patent No.: US 12,758,489 B2
(45) Date of Patent: Oct. 13, 2026

(54) BIO-INSPIRED TISSUE-ADHESIVE HYDROGEL PATCH FOR PREVENTING OR TREATING CARTILAGE OR BONE DISEASE

(71) Applicant: CELLARTGEN INC., Seoul (KR)

(72) Inventors: Seung Woo Cho, Seoul (KR); Soo Jeong Choi, Seoul (KR); Eun Je Jeon, Seoul (KR); Jong Seung Lee, Seoul (KR)

(73) Assignee: CELLARTGEN INC., Seoul (KR)

(*) Notice: Subject to any disclaimer, the term of this patent is extended or adjusted under 35 U.S.C. 154(b) by 743 days.

(21) Appl. No.: 18/176,890

(22) Filed: Mar. 1, 2023

(65) Prior Publication Data

US 2023/0201109 A1 Jun. 29, 2023

Related U.S. Application Data

(63) Continuation of application No. PCT/KR2021/011780, filed on Sep. 1, 2021.

(30) Foreign Application Priority Data

Sep. 1, 2020 (KR) ........................ 10-2020-0111332

(51) Int. Cl.

| | |
|---|---|
| ***A61K 31/728*** | (2006.01) |
| ***A61K 9/00*** | (2006.01) |
| ***A61K 9/06*** | (2006.01) |
| ***A61K 31/573*** | (2006.01) |
| ***A61K 38/18*** | (2006.01) |
| ***A61K 47/02*** | (2006.01) |
| ***A61K 47/36*** | (2006.01) |
| ***A61P 19/02*** | (2006.01) |
| ***A61P 19/08*** | (2006.01) |

(52) U.S. Cl.

CPC .............. *A61K 9/0024* (2013.01); *A61K 9/06* (2013.01); *A61K 31/573* (2013.01); *A61K 38/1875* (2013.01); *A61K 47/02* (2013.01); *A61K 47/36* (2013.01); *A61P 19/02* (2018.01); *A61P 19/08* (2018.01)

(58) Field of Classification Search

CPC ...... A61K 9/0024; A61K 9/06; A61K 31/573; A61K 38/1875; A61K 47/02; A61K 47/36; A61K 9/7084; A61K 9/7023; A61K 47/10; A61K 47/42; A61P 19/02; A61P 19/08; A61P 19/00

See application file for complete search history.

(56) References Cited

U.S. PATENT DOCUMENTS

| | | | | |
|---|---|---|---|---|
| 2011/0077216 | A1* | 3/2011 | Kastrup | A61K 47/60 536/18.7 |
| 2012/0156164 | A1 | 6/2012 | Park et al. | |
| 2018/0036337 | A1* | 2/2018 | Lorenzo-Zúñiga García | A61K 31/437 |

FOREIGN PATENT DOCUMENTS

| | | | |
|---|---|---|---|
| KR | 10-2011-0025530 | A | 3/2011 |
| KR | 10-2013-0133692 | A | 12/2013 |
| KR | 10-2019-0134576 | A | 12/2019 |
| KR | 10-2020-0017625 | A | 2/2020 |
| KR | 10-2021-0075051 | A | 6/2021 |
| WO | 2015174643 | A1 | 11/2015 |

OTHER PUBLICATIONS

Wang, D.; Xu, P.; Wang, S.; Li, W.; Liu. W. Rapidly curable hyaluronic acid-catechol hydrogels inspired by scallops as tissue adhesives for hemostasis and wound healing. European Polymer Journal, 134, 109763, 1-10. (Year: 2020).*

Soojeong Choi et al., "Osteoconductive hybrid hyaluronic acid hydrogel patch for effective bone formation", Journal of Controlled Release, vol. 327, Nov. 10, 2020, pp. 571-853.

Hyun Ji Park et al., "Catechol Functionalized Hyaluronic Acid Hydrogels Enhance Angiogenesis and Osteogenesis of Human Adipose Derived Stem Cells in Critical Tissue Defects", Biomacromolecules, vol. 17, issue 6, Apr. 25, 2016, pp. 1939-1948.

Jisoo Shin et al., "Tissue Tapes Phenolic Hyaluronic Acid Hydrogel Patches for Off the Shelf Therapy", Advanced Functional Materials, vol. 29, issue 49, Dec. 5, 2019, Article ID 1903863, pp. 1-15.

Li, H. et al. The Application of Hyaluronic Acid-Based Hydrogels in Bone and Cartilage Tissue Engineering. Hindawi Advances in Materials Science and Engineering. Dec. 20, 2019, vol. 2019, thesis No. 3027303, pp. 1-12.

* cited by examiner

*Primary Examiner* — Jessica Worsham

(74) *Attorney, Agent, or Firm* — NKL LAW; Jae Youn Kim

(57) ABSTRACT

The present disclosure relates to a hydrogel patch for preventing or treating cartilage or bone diseases, including: a hydrogel patch containing a biocompatible polymer functionalized with a phenol group; and a drug for treating cartilage or bone diseases loaded in the hydrogel patch.

7 Claims, 42 Drawing Sheets

HA-CA

HA-PG

| | Atomic composition (%) | | |
|---|---|---|---|
| | Patch | HAP-patch | WKT-patch |
| C1s | 60.29 | 48.31 | 34.59 |
| K2p | 0.68 | 0.15 | 0.1 |
| Ca2p | 0.48 | 3.45 | 6.48 |
| Mg2p | 0 | 0 | 2.75 |
| O1s | 36.62 | 41.75 | 47.25 |
| P2p | 1.93 | 6.34 | 8.83 |
| Total % | 100 | 100 | 100 |

BIO-INSPIRED TISSUE-ADHESIVE HYDROGEL PATCH FOR PREVENTING OR TREATING CARTILAGE OR BONE DISEASE

TECHNICAL FIELD

The present disclosure relates to a bio-inspired tissue-adhesive hydrogel patch (particularly, a phenol group-functionalized biocompatible polymer hydrogel patch) for preventing or treating cartilage or bone diseases.

BACKGROUND

Bones support soft tissues and the weight of the body and surround the internal organs to protect them from external shocks. Also, bones serve as one of the important parts of the body that not only support the muscles or organs, but also retain calcium or other essential minerals, i.e., phosphorus or magnesium.

Joints exist between bones of the body. Joints are classified into immovable joints that are found between two adjacent bones or cartilages, such as the skull or tooth roots, and permit very little or no mobility, movable joints that have a large amount of connective tissue between two bones, such as bones of the limbs or jaw of an animal, and permit high mobility, amphiarthrodial joints and semi-movable joints. Joints generally refer to the movable joints, and the movable joints are classified into ligamentous joints, whereby both bones are connected only with ligaments, and synovial joints. The synovial joint refers to a joint surrounded by a connective tissue capsule (articular capsule), and the inside of the articular capsule secretes a synovial fluid having lubricating properties, and many ligaments are located outside the articular capsule to strengthen the joint.

For the prevention or treatment of cartilage or bone diseases related to bones and joints, research using a hydrogel as a carrier for in vivo delivery of an anti-inflammatory agent or the like has been conducted. However, most of them relate to methods of loading an anti-inflammatory agent or the like in a hydrogel solution and inducing gel formation through cross-linking. However, such methods are performed by injecting a hydrogel into the body, and, thus, the results are likely to vary depending on a user's skill level in handling the hydrogel and the user's convenience is greatly reduced. Further, since the hydrogel is injected into the body by means of injection, there are still risks of tissue damage and bleeding, and most of conventional hydrogels have insufficient properties and adhesion to be maintained in vivo for a long time.

DISCLOSURE OF THE INVENTION

Problems to be Solved by the Invention

The present disclosure is intended to fabricate bio-inspired tissue-adhesive hydrogel patch which has excellent mechanical properties, tissue adhesion, biocompatibility and ease of use, and can effectively prevent or treat cartilage or bone diseases, and provides a hydrogel patch, including: a hydrogel patch containing a biocompatible polymer functionalized with a phenol group; and a drug for treating cartilage or bone diseases loaded in the hydrogel patch.

However, the problems to be solved by the present disclosure are not limited to the above-described problems. Although not described herein, other problems to be solved by the present disclosure can be clearly understood by a person with ordinary skill in the art from the following descriptions.

Means for Solving the Problems

An aspect of the present disclosure provides a hydrogel patch for preventing or treating cartilage or bone diseases, including: a hydrogel patch containing a biocompatible polymer functionalized with a phenol group; and a drug for treating cartilage or bone diseases loaded in the hydrogel patch.

In an embodiment of the present disclosure, the phenol group may be a catechol group derived from a catechol-based compound selected from the group consisting of catechol, 4-tert-butylcatechol (TBC), urushiol, alizarin, dopamine, dopamine hydrochloride, 3,4-dihydroxyphenylalanine (DOPA), caffeic acid, norepinephrine, epinephrine, 3,4-dihydroxyphenylacetic acid (DOPAC), isoprenaline, isoproterenol and 3,4-dihydroxybenzoic acid;

or a pyrogallol group derived from a pyrogallol-based compound selected from the group consisting of pyrogallol, 5-hydroxydopamine, tannic acid, gallic acid, epigallocatechin, epicatechin gallate, epigallocatechin gallate, 2,3,4-trihydroxybenzaldehyde, 2,3,4-trihydroxybenzoic acid, 3,4,5-trihydroxybenzaldehyde, 3,4,5-trihydroxybenzamide, 5-tert-butylpyrogallol and 5-methylpyrogallol.

In an embodiment of the present disclosure, the biocompatible polymer may be selected from the group consisting of hyaluronic acid, heparin, cellulose, dextran, alginate, chitosan, chitin, collagen, gelatin, chondroitin sulfate, pectin, keratin and fibrin.

In an embodiment of the present disclosure, the hydrogel patch may have i) a thickness of from 0.05 mm to 10.0 mm, ii) a storage modulus G' of from $1\times10^3$ Pa to $1\times10^6$ Pa in a frequency range of from 0.1 Hz to 10 Hz, iii) a friction factor of from 0.2 to 0.4 as measured at a speed of 0.01 m/s under a normal force of 5 N, and iv) an adhesive strength of from 10 kPa to 20 kPa.

In an embodiment of the present disclosure, the hydrogel patch may further contain inorganic mineral particles.

In an embodiment of the present disclosure, the inorganic mineral particles may include one or more inorganic ions selected from the group consisting of calcium, magnesium and phosphorus.

In an embodiment of the present disclosure, the inorganic ions may interact with the phenol group to form a complex compound through coordination bonding.

In an embodiment of the present disclosure, the inorganic ions may make ionic interactions with the drug.

In an embodiment of the present disclosure, the drug may contain an anti-inflammatory agent selected from the group consisting of dexamethasone, cortisone, prednisolone, hydrocortisone, triamcinolone, methylprednisolone, prednisone and betamethasone; or a bone morphogenetic protein selected from the group consisting of BMP-2 (BMP-2a), BMP-3 (osteogenin), BMP-4 (BMP-2b), BMP-6 (human homologue of the murine, Vgr-1), BMP-7 (osteogenic protein-1) and BMP-9 (growth differentiation factor 2).

In an embodiment of the present disclosure, the cartilage disease may be selected from the group consisting of inflammatory arthritis, degenerative arthritis, osteochondromatosis, distortion, bursitis, menstruation, meniscal tear, meniscus cyst, collateral ligament rupture, anterior cruciate ligament injury, posterior cruciate ligament injury, intraarticular vitreous, exfoliation osteochondritis, plica syndrome, genu varum, knock-knee and snapping knee, and the bone disease may be selected from the group consisting of growth retardation, osteopenia, osteopsathyrosis, osteonecrosis, fracture, osteoporosis due to excessive bone resorption by osteoclasts, osteogenesis imperfecta, bone damage, joint damage due to trauma, osteomalacia, rickets, fibrous osteitis, aplastic bone disease, metabolic bone disease, renal osteodystrophy, periodontal disease, Paget disease and metastatic bone cancers.

Effects of the Invention

A bio-inspired tissue-adhesive hydrogel patch (particularly, a phenol group-functionalized biocompatible polymer hydrogel patch) for preventing or treating cartilage or bone diseases according to the present disclosure has excellent mechanical properties, tissue adhesion, biocompatibility and ease of use compared with a solution-based bulk hydrogel, and enables effective sustained release of a drug for preventing or treating cartilage or bone disease in vivo and thus can induce a sustained therapeutic effect.

BEST MODE FOR CARRYING OUT THE INVENTION

Figure 1:
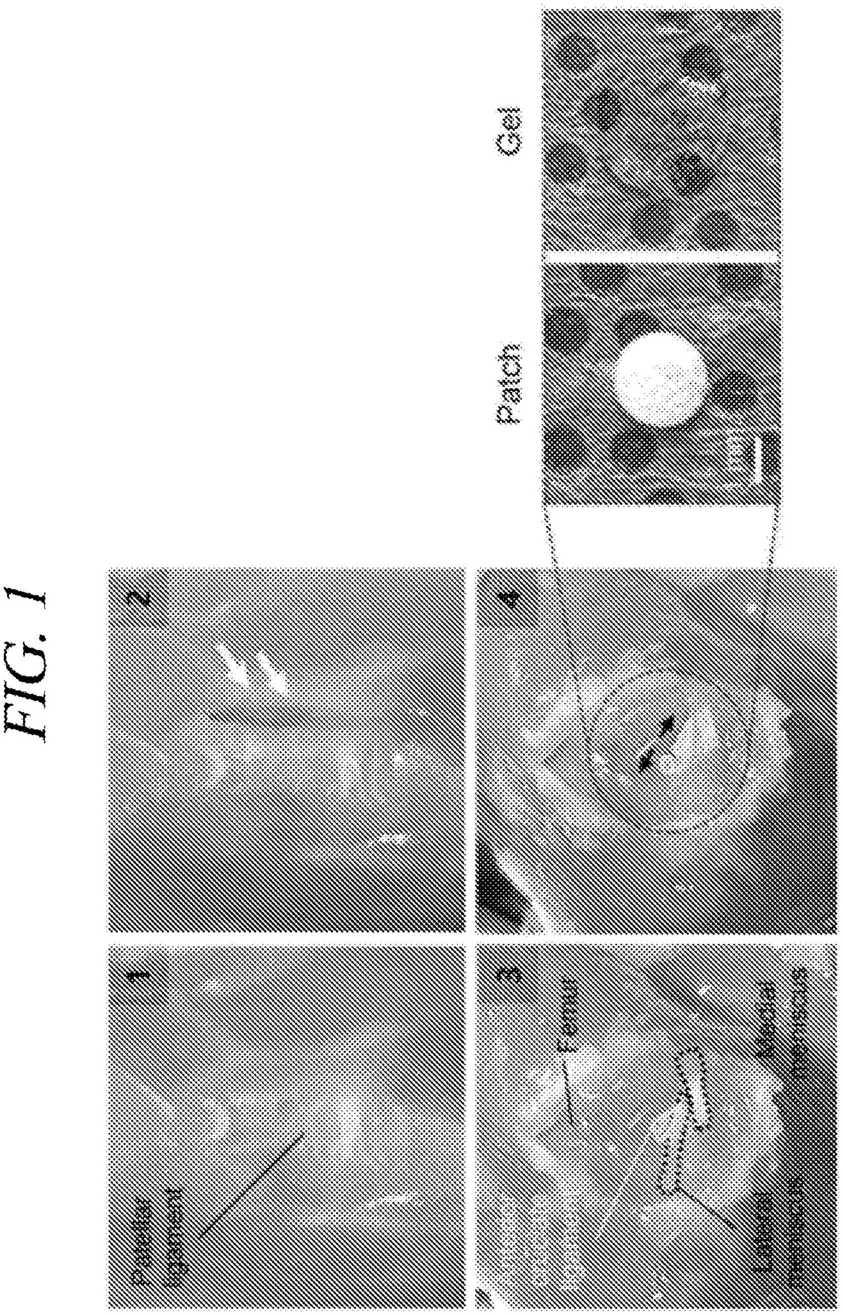
FIG. 1 shows where and how a phenol group-functionalized biocompatible polymer hydrogel patch is applied according to an embodiment of the present disclosure.

The present disclosure provides a hydrogel patch for preventing or treating cartilage or bone diseases, including: a hydrogel patch containing a biocompatible polymer functionalized with a phenol group; and a drug for treating cartilage or bone diseases loaded in the hydrogel patch.

The phenol group may be a catechol group derived from a catechol-based compound selected from the group consisting of catechol, 4-tert-butylcatechol (TBC), urushiol, alizarin, dopamine, dopamine hydrochloride, 3,4-dihydroxyphenylalanine (DOPA), caffeic acid, norepinephrine, epinephrine, 3,4-dihydroxyphenylacetic acid (DOPAC), isoprenaline, isoproterenol and 3,4-dihydroxybenzoic acid; or a pyrogallol group derived from a pyrogallol-based compound selected from the group consisting of pyrogallol, 5-hydroxydopamine, tannic acid, gallic acid, epigallocatechin, epicatechin gallate, epigallocatechin gallate, 2,3,4-trihydroxybenzaldehyde, 2,3,4-trihydroxybenzoic acid, 3,4,5-trihydroxybenzaldehyde, 3,4,5-trihydroxybenzamide, 5-tert-butylpyrogallol and 5-methylpyrogallol.

The biocompatible polymer may be selected from the group consisting of hyaluronic acid, heparin, cellulose, dextran, alginate, chitosan, chitin, collagen, gelatin, chondroitin sulfate, pectin, keratin and fibrin.

The hydrogel patch may have i) a thickness of from 0.05 mm to 10.0 mm, ii) a storage modulus G' of from $1\times10^3$ Pa to $1\times10^6$ Pa in a frequency range of from 0.1 Hz to 10 Hz, iii) a friction factor of from 0.2 to 0.4 as measured at a speed of 0.01 m/s under a normal force of 5 N, and iv) an adhesive strength of from 10 kPa to 20 kPa.

The hydrogel patch may further contain inorganic mineral particles.

The inorganic mineral particles may include one or more inorganic ions selected from the group consisting of calcium, magnesium and phosphorus.

The inorganic ions may interact with the phenol group to form a complex compound through coordination bonding, and the inorganic ions may make ionic interactions with the drug.

The drug may contain an anti-inflammatory agent selected from the group consisting of dexamethasone, cortisone, prednisolone, hydrocortisone, triamcinolone, methylprednisolone, prednisone and betamethasone; or a bone morphogenetic protein selected from the group consisting of BMP-2 (BMP-2a), BMP-3 (osteogenin), BMP-4 (BMP-2b), BMP-6 (human homologue of the murine, Vgr-1), BMP-7 (osteogenic protein-1) and BMP-9 (growth differentiation factor 2).

The cartilage disease may be selected from the group consisting of inflammatory arthritis, degenerative arthritis, osteochondromatosis, distortion, bursitis, menstruation, meniscal tear, meniscus cyst, collateral ligament rupture, anterior cruciate ligament injury, posterior cruciate ligament injury, intraarticular vitreous, exfoliation osteochondritis, plica syndrome, genu varum, knock-knee and snapping knee, and the bone disease may be selected from the group consisting of growth retardation, osteopenia, osteopsathyrosis, osteonecrosis, fracture, osteoporosis due to excessive bone resorption by osteoclasts, osteogenesis imperfecta, bone damage, joint damage due to trauma, osteomalacia, rickets, fibrous osteitis, aplastic bone disease, metabolic bone disease, renal osteodystrophy, periodontal disease, Paget disease and metastatic bone cancers.

The present inventors found that a bio-inspired tissue-adhesive hydrogel patch (particularly, a phenol group-functionalized biocompatible polymer hydrogel patch) has excellent mechanical properties, tissue adhesion, biocompatibility and ease of use and enables effective sustained release of a drug for preventing or treating cartilage or bone disease in vivo and thus is effective in preventing or treating cartilage or bone disease, and completed the present disclosure.

The present disclosure provides a hydrogel patch for preventing or treating cartilage or bone diseases, including: a hydrogel patch containing a biocompatible polymer functionalized with a phenol group; and a drug for treating cartilage or bone diseases loaded in the hydrogel patch.

The term "cartilage disease" used herein is selected from the group consisting of inflammatory arthritis, degenerative arthritis, osteochondromatosis, distortion, bursitis, menstruation, meniscal tear, meniscus cyst, collateral ligament rupture, anterior cruciate ligament injury, posterior cruciate ligament injury, intraarticular vitreous, exfoliation osteochondritis, plica syndrome, genu varum, knock-knee and snapping knee, and is desirably inflammatory arthritis, but is not limited thereto. The cartilage disease prevention or treatment efficacy can be confirmed by evaluating inflammatory arthritis treatment efficacy, ambulatory function improvement or cartilage damage reduction/cartilage tissue regeneration promotion.

The term "bone disease" used herein is selected from the group consisting of growth retardation, osteopenia, osteopsathyrosis, osteonecrosis, fracture, osteoporosis due to excessive bone resorption by osteoclasts, osteogenesis imperfecta, bone damage, joint damage due to trauma, osteomalacia, rickets, fibrous osteitis, aplastic bone disease, metabolic bone disease, renal osteodystrophy, periodontal disease, Paget disease and metastatic bone cancers. The bone disease prevention or treatment efficacy can be confirmed by verifying bone differentiation promoting effect or evaluating efficacy in treating a bone defect model. Here, the bone differentiation promoting effect can be confirmed by checking whether the expression of bone differentiation markers such as collagen type 1 (Col1), runt-related transcription factor 2 (RUNX2), osteopontin (OPN) and osteocalcin (OCN) is increased, or checking the degree of calcium deposition after stem cell bone differentiation.

First, the hydrogel patch for preventing or treating cartilage or bone diseases according to the present disclosure includes a hydrogel patch containing a biocompatible polymer functionalized with a phenol group.

As used herein, the term "phenol group" is a functional group derived from a phenol-based compound, desirably a functional group derived from a catechol-based compound including 1,2-dihydroxybenzene having two hydroxyl groups (—OH) located adjacent to each other or a functional group derived from a pyrogallol-based compound including 1,2,3-trihydroxybenzene having three hydroxyl groups (—OH) located adjacent to each other, at the terminal. The phenol group can form covalent cross-linking with various functional groups through an oxidation reaction. The phenol group can optionally interact with inorganic ions to be described later in an oxidized state. Specifically, the two adjacent hydroxyl groups (—OH) may form a complex compound through coordination bonding with inorganic ions to be described later (e.g., inorganic ion ($Ca^{2+}$, $Mg^{2+}$, etc.)-oxide coordination bonding) in an oxidized state, and more specifically, two adjacent hydroxyl groups (—OH) and functionalizing a biocompatible polymer and two adjacent hydroxyl groups (—OH) and functionalizing another biocompatible polymer may act as four ligands in an oxidized state to form a complex compound through coordination bonding with inorganic ions to be described later. As a result, phenol groups functionalizing different biocompatible polymers can be cross-linked by inorganic ions. Desirably, the hydrogel patch may further include a terminal functional group for reaction with the biocompatible polymer in addition to the phenol group, but is not limited thereto.

Specifically, the catechol-based compound may be selected from the group consisting of catechol, 4-tert-butylcatechol (TBC), urushiol, alizarin, dopamine, dopamine hydrochloride, 3,4-dihydroxyphenylalanine (DOPA), caffeic acid, norepinephrine, epinephrine, 3,4-dihydroxyphenylacetic acid (DOPAC), isoprenaline, isoproterenol and 3,4-dihydroxybenzoic acid. In the present disclosure, dopamine hydrochloride is used as a catechol-based compound, and in this case, —$NH_2$ in a terminal functional group of dopamine hydrochloride may react with the biocompatible polymer (particularly, hyaluronic acid).

Also, the pyrogallol-based compound may be selected from the group consisting of pyrogallol, 5-hydroxydopamine, tannic acid, gallic acid, epigallocatechin, epicatechin gallate, epigallocatechin gallate, 2,3,4-trihydroxybenzaldehyde, 2,3,4-trihydroxybenzoic acid, 3,4,5-trihydroxybenzaldehyde, 3,4,5-trihydroxybenzamide, 5-tert-butylpyrogallol and 5-methylpyrogallol. In the present disclosure, 5-hydroxydopamine is used as a pyrogallol-based compound, and in this case, —$NH_2$ in a terminal functional group of 5-hydroxydopamine may react with the biocompatible polymer (particularly, hyaluronic acid).

In particular, a pyrogallol group used as a phenol group can be naturally oxidized within minutes without treatment of an oxidizing agent in an environment with high oxygen concentration, such as in the living body, due to its rapid oxidizing properties. Therefore, when the hydrogel patch is actually applied to clinical practice, it can be directly applied without treatment of an oxidizing agent.

As used herein, the term "biocompatible polymer" may react with a terminal functional group present in the phenol-based compound so as to be functionalized with the phenol group. Specifically, the biocompatible polymer may be selected from the group consisting of hyaluronic acid, heparin, cellulose, dextran, alginate, chitosan, chitin, collagen, gelatin, chondroitin sulfate, pectin, keratin and fibrin, and may be desirably hyaluronic acid and may be more desirably hyaluronic acid having a molecular weight of from 100 kDa to 10 MDa, but is not limited thereto. In that case, —COOH in a terminal functional group of hyaluronic acid may react with the phenol-based compound.

As used herein, the term "hydrogel patch" refers to a structure formed into a thin film having a predetermined thickness and including a biocompatible polymer functionalized with a phenol group, and can be cut or molded into a desired shape by a known method and thus is convenient to use. The hydrogel patch has excellent mechanical properties, tissue adhesion, biocompatibility and ease of use compared with a solution-based bulk hydrogel.

Specifically, the hydrogel patch may be prepared by the following processes:

(a) a process of pouring a biocompatible polymer solution functionalized with a phenol group evenly on a flat surface; and (b) a process of freeze-drying the solution at −0.5° C. to −100° C. for 5 hours to 48 hours.

Specifically, the process (a) may be performed by pouring 40 μl to 200 μl of a biocompatible polymer solution functionalized with a phenol group into a cylindrical mold, and the biocompatible polymer solution functionalized with a phenol group may be used at a concentration of from 0.1 (w/v) % to 5 (w/v) % and desirably of from 0.5 (w/v) % to 3 (w/v) %. The amount of the biocompatible polymer solution functionalized with a phenol group is required to form a hydrogel patch having a thickness of from 0.8 mm to 3.2 mm, and the thickness of the hydrogel patch can be easily regulated.

Further, the process (b) may be performed by freeze-drying the biocompatible polymer solution functionalized with a phenol group at −0.5° C. to −100° C. for 5 hours to 48 hours, or desirably by freeze-drying at −50° C. to −100° C. for 12 hours to 36 hours. When the biocompatible polymer solution functionalized with a phenol group is freeze-dried, the volume of the solution is decreased and a hydrogel patch in the form of a thin film having a predetermined thickness is formed.

As a result, the hydrogel patch may have i) a thickness of from 0.05 mm to 10.0 mm, desirably from 0.1 mm to 5.0 mm and more desirably from 1.6 mm to 5.0 mm, ii) a storage modulus G' of from $1\times10^3$ Pa to $1\times10^6$ Pa, desirably from $1\times10^4$ Pa to $1\times10^6$ Pa and more desirably from $3\times10^4$ Pa to $1\times10^6$ Pa in a frequency range of from 0.1 Hz to 10 Hz, iii) a friction factor of from 0.2 to 0.4 as measured at a speed of 0.01 m/s under a normal force of 5 N, and iv) an adhesive strength of from 10 kPa to 20 kPa and desirably from 13 kPa to 15 kPa. If the hydrogel patch is a pyrogallol group-functionalized biocompatible polymer hydrogel patch and particularly inorganic mineral particles (particularly, whitlockite) are added thereto, the mechanical properties thereof can be further improved.

The hydrogel patch may further contain inorganic mineral particles, and inorganic ions released from the inorganic mineral particles can make ionic interactions with the phenol group or the drug for preventing or treating cartilage or bone diseases. Therefore, its efficacy as well as mechanical properties can be further improved. The inorganic mineral particles may be added at a concentration of from 0.1 (w/v) % to 10 (w/v) % and desirably from 0.5 (w/v) % to 5 (w/v) % into the biocompatible polymer solution functionalized with a phenol group. That is, the weight ratio of the phenol group-functionalized biocompatible polymer and the inorganic mineral particles may be from 1:1 to 1:100 and desirably from 1:1 to 1:5.

Specifically, the inorganic mineral particles may include one or more inorganic ions selected from the group consisting of calcium, magnesium and phosphorus, and such inorganic ions may help bone regeneration. For example, if the inorganic mineral particles are hydroxyapatite or whitlockite, they contain calcium and phosphorus and thus can release calcium and phosphorus. If the inorganic mineral particles are whitlockite, magnesium can be additionally released. Calcium or magnesium among the inorganic ions has a cationic surface charge and thus can interact with the oxidized phenol group. Specifically, calcium or magnesium among the inorganic ions may form a complex compound through coordination bonding with the two adjacent hydroxyl groups (—OH) (e.g., inorganic ion ($Ca^{2+}$, $Mg^{2+}$, etc.)-oxide coordination bonding) in an oxidized state, and more specifically, two adjacent hydroxyl groups (—OH) and functionalizing a biocompatible polymer and two adjacent hydroxyl groups (—OH) and functionalizing another biocompatible polymer may act as four ligands in an oxidized state to form a complex compound through coordination bonding with calcium or magnesium among the inorganic ions. As a result, the inorganic ions can cross-link phenol groups functionalizing different biocompatible polymers.

Accordingly, the mechanical properties thereof can be improved. Further, phosphorus among the inorganic ions has an anionic surface charge and thus can make an ionic interaction with the drug for preventing or treating cartilage or bone diseases (particularly, bone morphogenetic protein) to be described later, allowing sustained release of the drug.

Also, the hydrogel patch for preventing or treating cartilage or bone diseases according to the present disclosure includes the drug for preventing or treating cartilage or bone diseases loaded in the hydrogel patch. The amount of the drug for preventing or treating cartilage or bone diseases may be from 0.002 wt % to 10 wt % and desirably from 0.002 wt % to 4 wt % based on the total amount of the hydrogel patch, but is not limited thereto. In other words, 100 ng to 2 mg of the drug for preventing or treating cartilage or bone diseases can be loaded in each hydrogel patch (based on a diameter of from 0.05 mm to 10.0 mm and a thickness of from 0.05 mm to 10.0 mm and desirably based on a diameter of from 0.1 mm to 5.0 mm and a thickness of from 0.1 mm to 5.0 mm).

It can be effectively released in a sustained manner in vivo and thus can induce a lasting therapeutic effect. Various nucleophilic functional groups may exist in the drug for preventing or treating cartilage or bone diseases and may form a strong bond with the oxidized phenol group.

Specifically, the drug for preventing or treating cartilage diseases may be an anti-inflammatory agent selected from the group consisting of dexamethasone, cortisone, prednisolone, hydrocortisone, triamcinolone, methylprednisolone, prednisone and betamethasone. In particular, if a corticosteroid-based anti-inflammatory agent, such as dexamethasone, is loaded for preventing or treating cartilage diseases, it has excellent loading efficiency and excellent inflammatory arthritis treatment efficacy and can improve ambulatory function, reduce cartilage damage and promote cartilage tissue regeneration. Nucleophilic functional groups (carboxyl group, hydroxyl group, etc.) present in the anti-inflammatory agent can form a strong bond with the oxidized phenol group and thus can be effectively released in a sustained manner in vivo.

The drug for preventing or treating cartilage or bone diseases (particularly, bone morphogenetic protein) may make ionic interactions with phosphorus among the inorganic ions.

Specifically, a method of loading a drug for preventing or treating cartilage or bone diseases in the hydrogel patch may be performed by mixing a biocompatible polymer solution functionalized with a phenol group and a drug for preventing or treating cartilage or bone diseases to fabricate a hydrogel patch, or by applying a drug for preventing or treating cartilage or bone diseases onto a phenol group-functionalized biocompatible polymer hydrogel patch and then cross-linking the drug to the phenol group-functionalized biocompatible polymer hydrogel patch through treatment of an oxidizing agent. In this case, the treatment of the oxidizing agent may be performed by applying or spraying an oxidizing agent solution to a hydrogel patch applied with the drug for preventing or treating cartilage or bone diseases. However, if the hydrogel patch is functionalized with a pyrogallol group, it is naturally oxidized in vivo without treatment of an oxidizing agent and thus is easy to use in actual clinical practice.

In particular, if an anti-inflammatory agent, such as dexamethasone, is loaded for preventing or treating cartilage diseases, it has excellent inflammatory arthritis treatment efficacy and can improve ambulatory function, reduce cartilage damage and promote cartilage tissue regeneration. Meanwhile, if a bone morphogenetic protein is loaded for preventing or treating bone diseases, it has bone differentiation promoting effect and can promote bone regeneration.

Moreover, if inorganic mineral particles (particularly, whitlockite) are added into the hydrogel patch, inorganic ions released from the inorganic mineral particles can make ionic interactions with the phenol group or the drug for preventing or treating cartilage or bone diseases. Therefore, its efficacy as well as mechanical properties can be further improved.

MODE FOR CARRYING OUT THE INVENTION

Hereafter, one or more specific examples will be described in more detail. However, these examples are provided for illustrative purposes only and the scope of the present disclosure is not limited to these examples.

Preparation Example 1

(1) Fabrication of HA-CA Hydrogel Patch

A catechol-functionalized hyaluronic acid with dopamine hydrochloride (hereinafter, referred to as HA-CA) (molecular weight=200 kDa) was dissolved in distilled water at a concentration of 1 (w/v) % dopamine hydrochloride, and 80 μl of the 1 (w/v) % HA-CA solution was poured into an 8 mm cylindrical mold and then freeze-dried overnight at −80° C. to fabricate an HA-CA hydrogel patch with a diameter of 8 mm and a thickness of 1.6 mm. The fabricated HA-CA hydrogel patch is in a dry state and thus is easy to store. Also, it is fabricated in the form of a thin film and thus can be easily cut into a desired shape. Therefore, it is convenient to use.

Meanwhile, HA-CA was dissolved in phosphate-buffered saline (PBS), and a 4.5 mg/ml sodium periodate solution was added into the solution to fabricate an HA-CA bulk hydrogel. A final concentration of HA-CA in the fabricated HA-CA bulk hydrogel was 1 (w/v) % (FIG. 1).

(2) Analysis on Physical Properties of HA-CA Hydrogel Patch

Figure 2A:
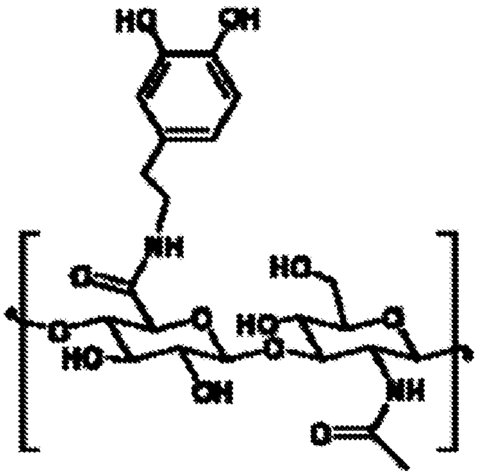
FIG. 2A shows the structural formula of HA-CA.
Figure 2B:
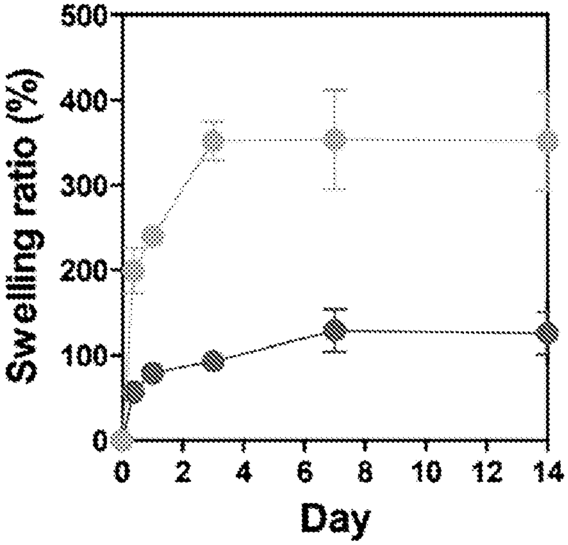
FIG. 2B shows the result of analyzing a swelling ratio of an HA-CA hydrogel patch.

The HA-CA hydrogel patch or the HA-CA bulk hydrogel was immersed in PBS at 37° C. similar to in vivo conditions for 14 days, and the swelling ratio was measured after 12 hours, 1 day, 3 days, 7 days and 14 days. As a result of measurement, the swelling ratio of the HA-CA hydrogel patch (Patch) was higher than that of the HA-CA bulk hydrogel (Gel) (FIG. 2B).

Figure 2C:
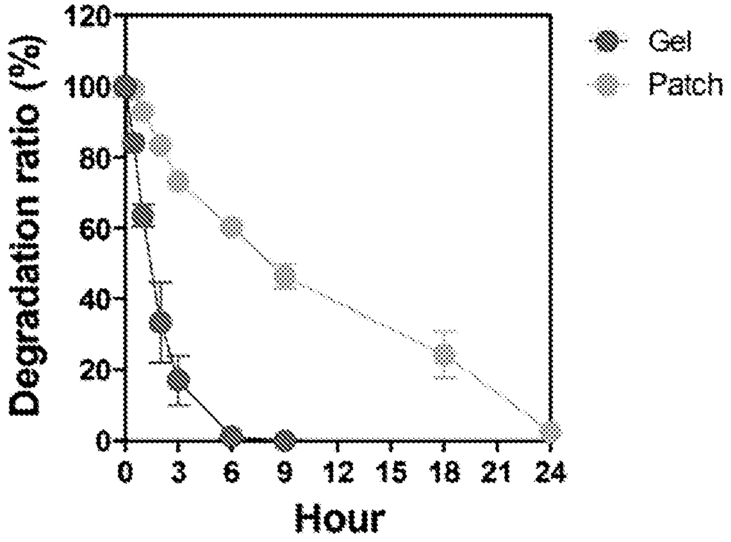
FIG. 2C shows the result of analyzing a degradation rate of the HA-CA hydrogel patch by an enzyme.

Since various degrading enzymes exist in the actual in vivo environment, the HA-CA hydrogel patch or the HA-CA bulk hydrogel was immersed in PBS at 37° C. and then treated with a hyaluronidase until degradation (100 U/sample). The weight of the HA-CA hydrogel patch or the HA-CA bulk hydrogel was measured at regular time intervals to measure the degrees of degradation over time. As a result of measurement, the HA-CA bulk hydrogel (Gel) was rapidly degraded within 2 hours after the treatment with the hyaluronidase and completely degraded after 6 hours. However, the HA-CA hydrogel patch (Patch) remained even after 24 hours from the treatment with the hyaluronidase. Thus, it was found that the degradation rate by the enzyme decreased (FIG. 2C).

Therefore, the HA-CA hydrogel patch is expected to maintain its shape well when applied to cartilage treatment and show sustained release of a loaded drug upon degradation.

(3) Analysis on Mechanical Properties of HA-CA Hydrogel Patch

Figure 3A:
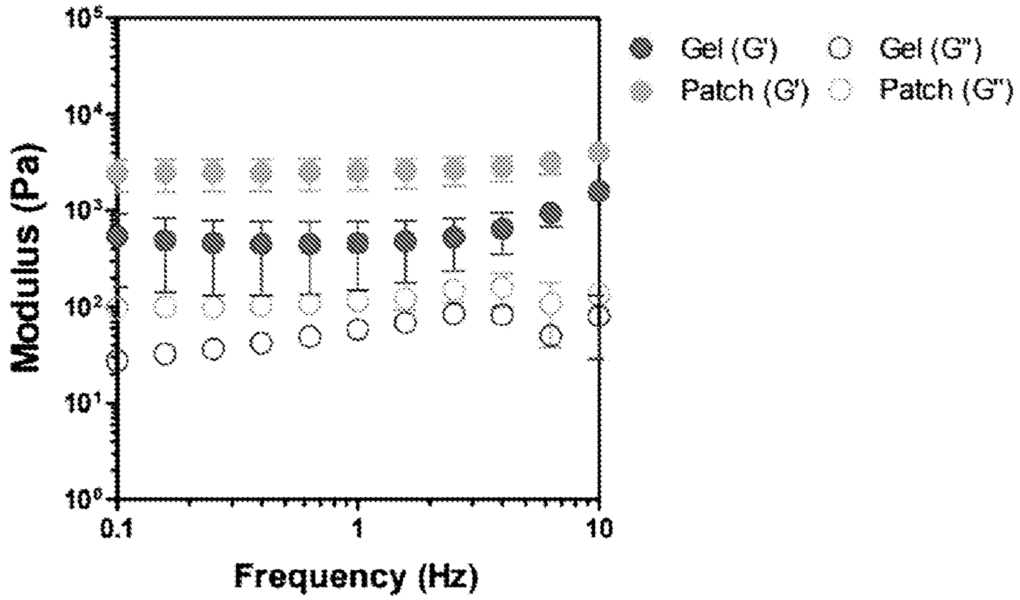
FIG. 3A shows the result of measuring a storage modulus and a loss modulus of the HA-CA hydrogel patch.

The elastic modulus of the HA-CA hydrogel patch or the HA-CA bulk hydrogel was measured at a frequency of from 0.1 Hz and 10 Hz by using a rheometer. As a result of analysis, both the HA-CA hydrogel patch (Patch) and the HA-CA bulk hydrogel (Gel) showed higher storage moduli G' than loss moduli G". Thus, it was found that the internal structure is formed of a stable polymer network (FIG. 3A).

Figure 3B:
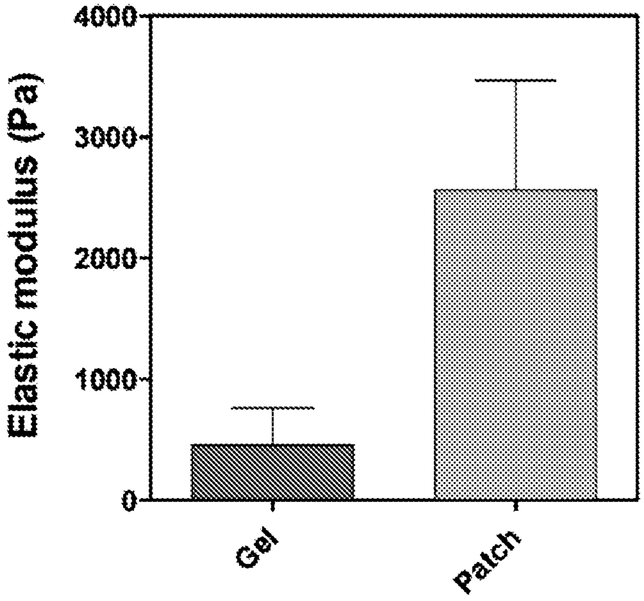
FIG. 3B shows the result of measuring an average storage modulus of the HA-CA hydrogel patch.
Figure 3C:
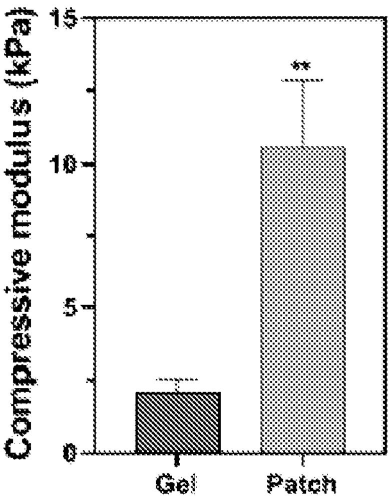
FIG. 3C shows the result of measuring the indentation strength of the HA-CA hydrogel patch.

Further, the average storage modulus G' of the HA-CA bulk hydrogel (Gel) was about 450 Pa, whereas the average storage modulus G' of the HA-CA hydrogel patch (Patch) was in the range of from about 2500 Pa to about 2600 Pa. Thus, it was found that the average storage modulus G' increased by about 5 times or more (FIG. 3B). Furthermore, when the indentation strength of HA-CA bulk hydrogel (Gel) and the HA-CA hydrogel patch (Patch) was measured, it was found that the indentation strength of the HA-CA hydrogel patch (Patch) was significantly high (FIG. 3C).

Therefore, the HA-CA hydrogel patch is expected to serve as a buffer to reduce damage caused by wear of cartilage tissues in addition to its role as a drug delivery system.

Figure 4A:
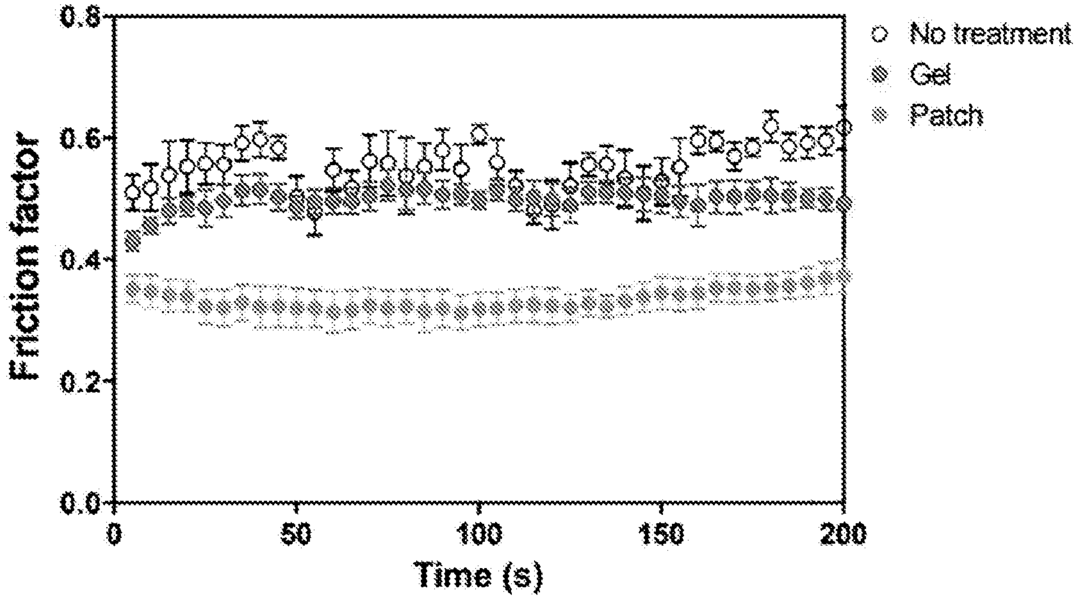
FIG. 4A shows the result of analyzing a friction factor of the HA-CA hydrogel patch.
Figure 4B:
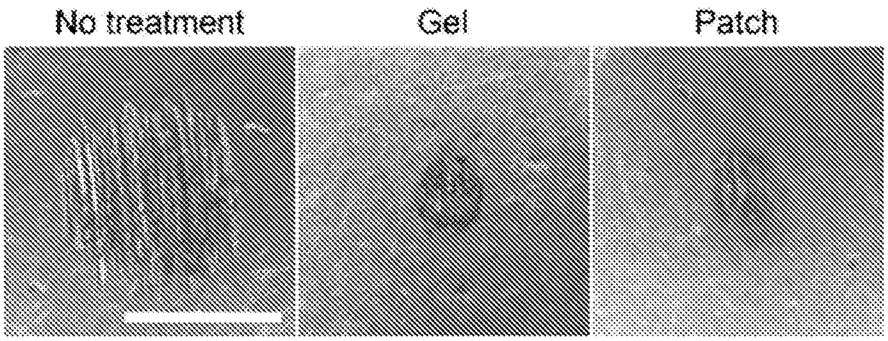
FIG. 4B shows the result of analyzing the degree of wear scar of the HA-CA hydrogel patch.
Figure 4C:
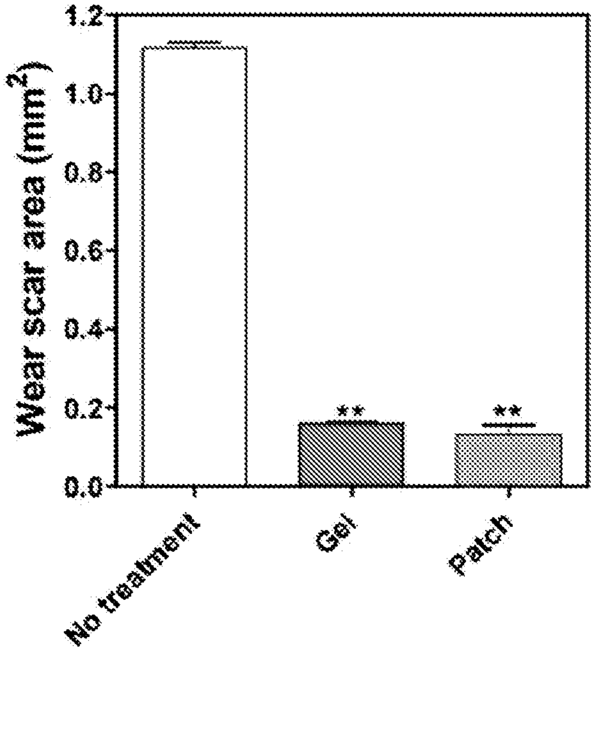
FIG. 4C shows the result of analyzing the area of wear scar of the HA-CA hydrogel patch.

Meanwhile, a friction factor was measured by moving a friction force analyzer at a speed of 0.01 m/s in a state where a normal force of 5 N was applied between stainless steel surfaces coated with the HA-CA hydrogel patch or the HA-CA bulk hydrogel. As a result of measurement, the friction factor was the highest in the case of no coating (No treatment), followed by the HA-CA bulk hydrogel (Gel) and the HA-CA hydrogel patch (Patch) (FIG. 4A). Further, in the case of no coating (No treatment), a large wear scar was formed due to friction, and in the HA-CA bulk hydrogel (Gel) and the HA-CA hydrogel patch (Patch), a small wear scar was formed (FIG. 4B). Therefore, in the HA-CA bulk hydrogel (Gel) and the HA-CA hydrogel patch (Patch), the area of wear scar was significantly reduced compared with the case of no coating (No treatment) (FIG. 4C).

Therefore, the HA-CA hydrogel patch is expected to serve as a buffer to improve wear resistance by reducing friction between joints.

Example 1

(1) Evaluation of Sustained Drug Release Pattern of Dexamethasone-Loaded HA-CA Hydrogel Patch When an HA-CA hydrogel patch or HA-CA bulk hydrogel was prepared according to Preparation Example 1, an HA-CA solution added with dexamethasone was used (dexamethasone content per patch=0.5 mg). Then, a 4.5 mg/ml sodium periodate solution was applied, followed by checking a sustained drug release pattern.

Figure 5:
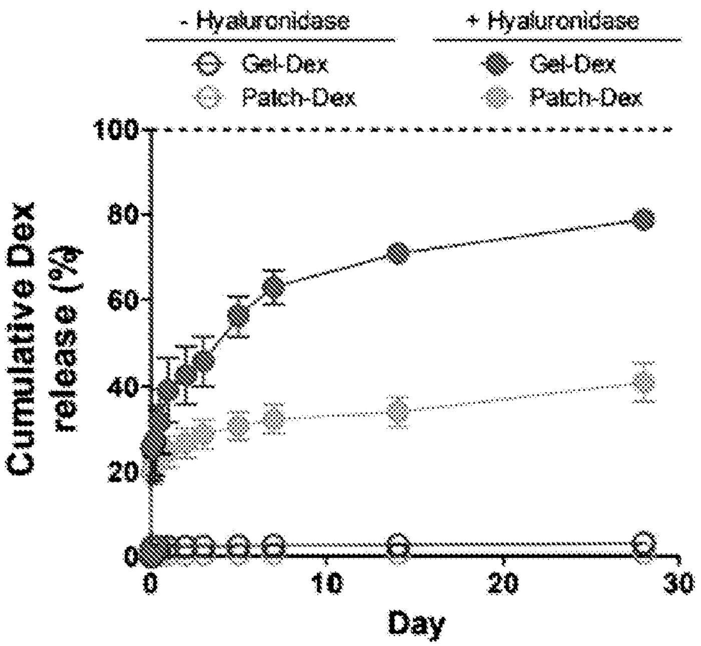
FIG. 5 shows the result of evaluating a sustained drug release pattern of a dexamethasone-loaded HA-CA hydrogel patch.

Thereafter, the HA-CA hydrogel patch or HA-CA bulk hydrogel loaded with dexamethasone was immersed in PBS at 37° C. and then treated with a hyaluronidase until degradation (100 U/sample). As a result of evaluation of the sustained drug release pattern by UV-vis analysis, release of dexamethasone hardly occurred in an environment without any degradative enzyme due to strong bonds between catechol groups and various nucleophilic functional groups of proteins, but it was found that the drug was effectively released when treated with a degradative enzyme in a bio-inspired environment. In particular, a hydrogel in the form of a gel is degraded at a higher rate than a hydrogel in the form of a patch. Thus, it was confirmed that the dexamethasone-loaded HA-CA hydrogel patch (Patch-Dex) can release dexamethasone in a sustained manner compared with the dexamethasone-loaded HA-CA bulk hydrogel (Gel-Dex) (FIG. 5).

Therefore, when the HA-CA hydrogel patch loaded with a drug is applied to a disease site, such as an inflammation site, where the activity of a hyaluronidase is increased, it is expected to induce a sustained therapeutic effect through effective sustained drug release.

(2) Evaluation of Inflammatory Arthritis Treatment Efficacy, Ambulatory Function Improvement and Cartilage Damage Reduction/Cartilage Tissue Regeneration Promotion of Dexamethasone-Loaded HA-CA Hydrogel Patch Inflammatory arthritis was induced by cutting the anterior cruciate ligament of each mouse. The cut site was treated with a dexamethasone-loaded HA-CA hydrogel patch or HA-CA bulk hydrogel (dexamethasone content per mouse=0.5 mg).

Figure 6:
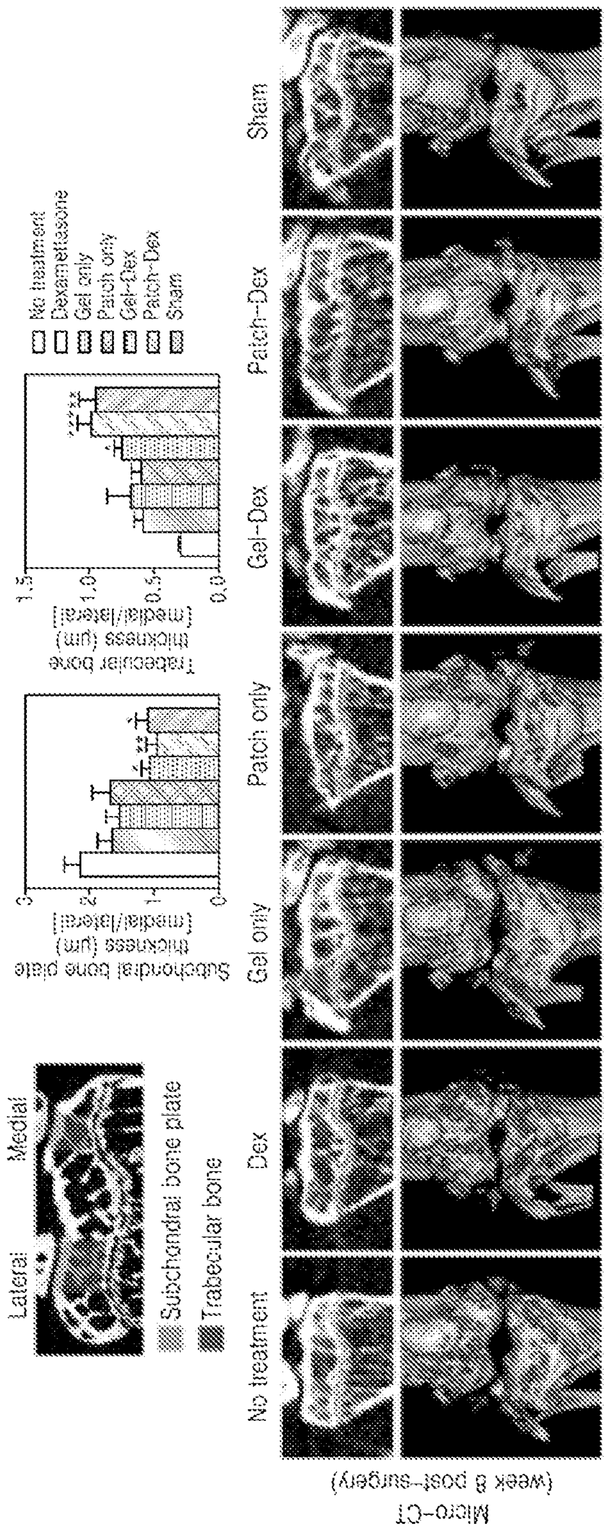
FIG. 6 shows the result of evaluating inflammatory arthritis treatment efficacy of the dexamethasone-loaded HA-CA hydrogel patch.

As a result of evaluation of inflammatory arthritis treatment efficacy by micro-CT after 8 weeks, in the case of no treatment (No treatment), the subchondral bone plate of the knee joint increased in thickness or the trabecular bone (in red) layer decreased in thickness, and the meniscus (red arrows) was abnormally damaged. In the case of treatment with dexamethasone (Dexamethasone), the HA-CA bulk hydrogel (Gel only) or the HA-CA hydrogel patch (Patch only), tissue damage was partially reduced, but the therapeutic effect was not significant. However, in the case of treatment with the dexamethasone-loaded HA-CA bulk hydrogel (Gel-Dex) or the dexamethasone-loaded HA-CA hydrogel patch (Patch-Dex), sustained release of dexamethasone was induced at the site of inflammatory arthritis, and, thus, the treatment efficacy was improved and tissue damage was minimized. Particularly, in the case of treatment with the dexamethasone-loaded HA-CA hydrogel patch (Patch-Dex), tissue regeneration was induced to the level of the normal group (Sham) (FIG. 6).

Figure 7:
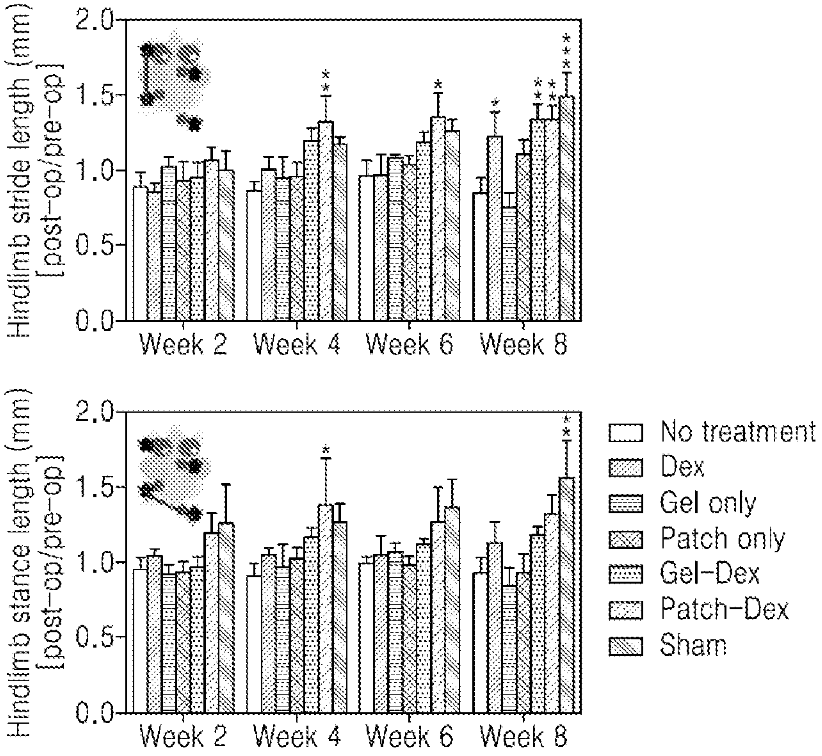
FIG. 7 shows the result of evaluating ambulatory function improvement by the dexamethasone-loaded HA-CA hydrogel patch.

Meanwhile, in order to evaluate improvement in ambulatory function, analysis on ambulatory function of the mice was performed every 2 weeks for 8 weeks. As a result of analyzing the stride length and the stance length, in the case of treatment with dexamethasone (Dex), the dexamethasone-loaded HA-CA bulk hydrogel (Gel-Dex) or the dexamethasone-loaded HA-CA hydrogel patch (Patch-Dex), the ambulatory function was improved. Particularly, in the case of treatment with the dexamethasone-loaded HA-CA hydrogel patch (Patch-Dex), a significant improvement in ambulatory function was induced to the level of the normal group (Sham) (FIG. 7).

Figure 8:
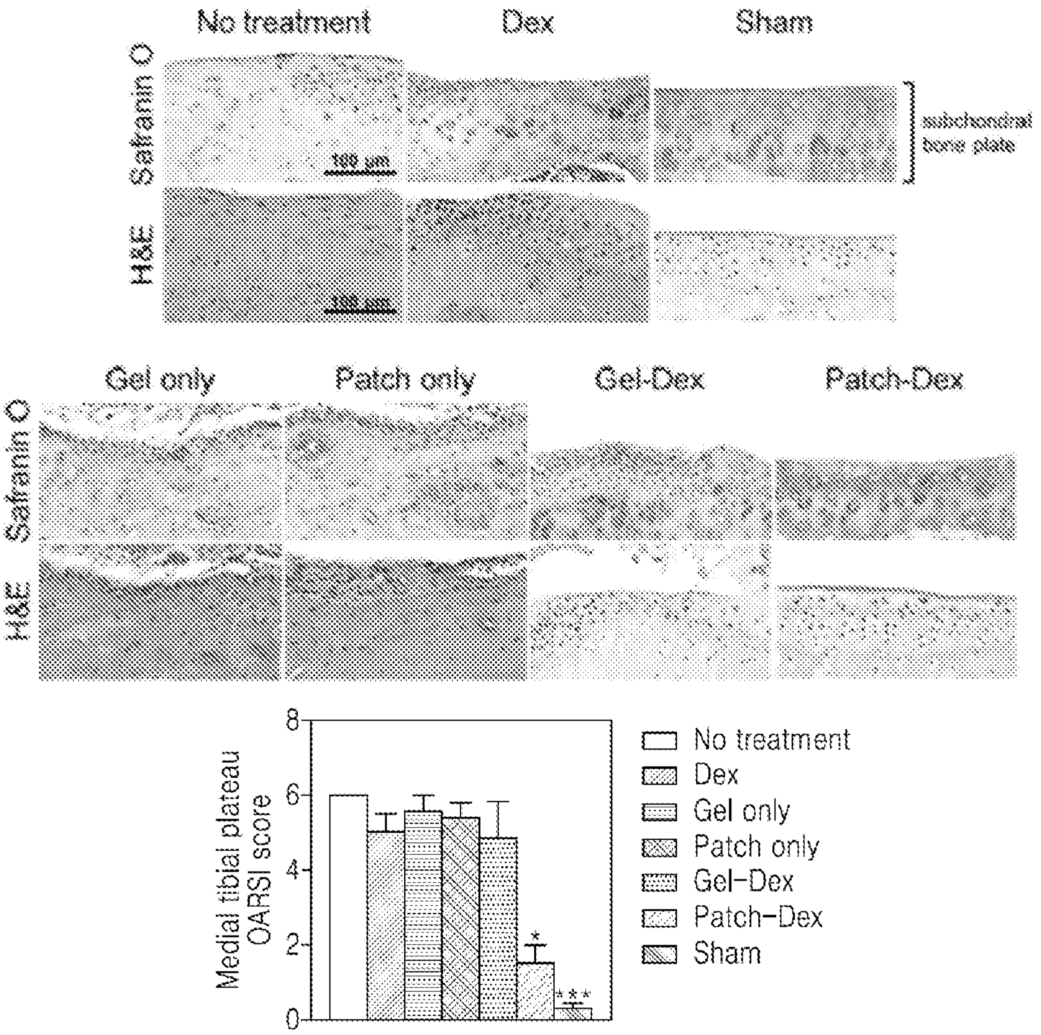
FIG. 8 shows the result of evaluating cartilage damage reduction/cartilage tissue regeneration promotion by the dexamethasone-loaded HA-CA hydrogel patch.

Meanwhile, in order to evaluate reduction in cartilage damage/promotion of cartilage tissue regeneration, histological analysis was performed after 8 weeks. Specifically, changes in the expression level of proteoglycan in the articular surface (red part in the result of Safranin O staining), changes in cell arrangement, changes in cartilage tissue, and damage patterns were analyzed by Safranin O staining and hematoxylin & eosin staining. As a result of analysis, in the case of no treatment (No treatment), the thickness of the subchondral bone plate increased abnormally, and in the case of treatment with dexamethasone (Dex), the HA-CA bulk hydrogel (Gel only) or the HA-CA hydrogel patch (Patch only), the thickness of the sublingual bone plate was partially reduced, but cartilage damage and extracellular matrix loss were not recovered (Osteoarthritis Research Society International score; OARSI score). However, in the case of treatment with the dexamethasone-loaded HA-CA hydrogel patch (Patch-Dex), the osteoarthritis treatment efficacy was greatly improved and cartilage tissue regeneration was induced to the level of the normal group (Sham) due to sustained release of dexamethasone and supply of hyaluronic acid (FIG. 8).

Preparation Example 2

(1) Fabrication of HA-PG Hydrogel Patch

A pyrogallol-functionalized hyaluronic acid with 5-hydroxydopamine (hereinafter, referred to as HA-PG) (molecular weight=200 kDa and 1 MDa) was dissolved in distilled water at a concentration of 1 (w/v) %, and 80 μl of the 1 (w/v) % HA-PG solution was poured into an 8 mm cylindrical mold and then freeze-dried overnight at −80° C. to fabricate an HA-PG hydrogel patch with a diameter of 8 mm and a thickness of 1.6 mm. The fabricated HA-PG hydrogel patch is in a dry state and thus is easy to store. Also, it is fabricated in the form of a thin film and thus can be easily cut into a desired shape. Therefore, it is convenient to use.

Meanwhile, HA-PG was dissolved in phosphate-buffered saline (PBS), and a 4.5 mg/ml sodium periodate solution was added into the solution to fabricate an HA-PG bulk hydrogel. A final concentration of HA-PG in the fabricated HA-PG bulk hydrogel was 1 (w/v) % (FIG. 1).

(2) Analysis on Physical Properties of HA-PG Hydrogel Patch

Figure 9A:
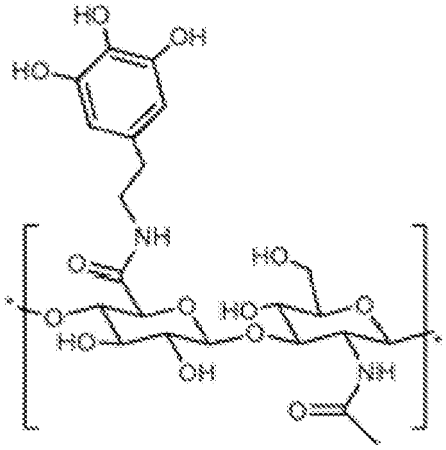
FIG. 9A shows the structural formula of HA-PG.
Figure 9B:
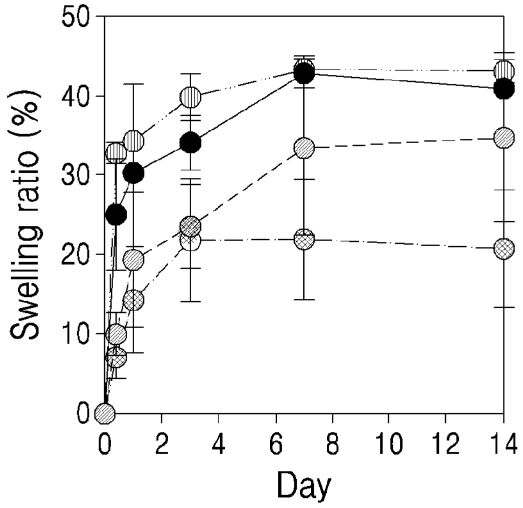
FIG. 9B shows the result of analyzing a swelling ratio of an HA-PG hydrogel patch.

The HA-PG hydrogel patch or the HA-PG bulk hydrogel was immersed in PBS at 37° C. similar to in vivo conditions for 14 days, and the swelling ratio was measured after 12 hours, 1 day, 3 days, 7 days and 14 days. As a result of measurement, the swelling ratio of the HA-PG hydrogel patch (Patch) was higher than that of the HA-PG bulk hydrogel (Gel) (FIG. 9B).

Figure 9C:
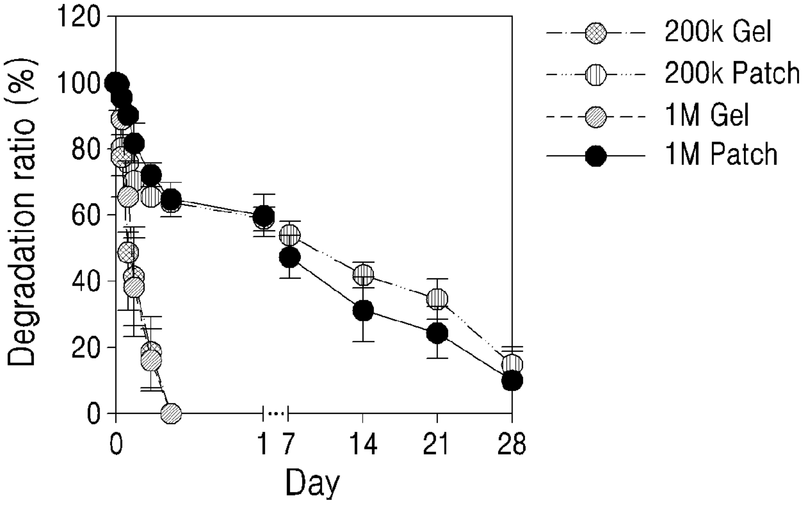
FIG. 9C shows the result of analyzing a degradation rate of the HA-PG hydrogel patch by an enzyme.

Since various degrading enzymes exist in the actual in vivo environment, the HA-PG hydrogel patch or the HA-PG bulk hydrogel was immersed in PBS at 37° C. and then treated with a hyaluronidase until degradation (200 U/sample). The weight of the HA-PG hydrogel patch or the HA-PG bulk hydrogel was measured at regular time intervals to measure the degrees of degradation over time. As a result of measurement, the HA-PG bulk hydrogels (200 kDa and 1 MDa Gels) were rapidly degraded at an early stage after the treatment with the hyaluronidase. However, the HA-PG hydrogel patches (200 kDa and 1 MDa Patches) remained even after 28 days from the treatment with the hyaluronidase. Thus, it was found that the degradation rate by the enzyme decreased considerably (FIG. 9C).

Therefore, the HA-PG hydrogel patch is expected to maintain its shape well when applied to cartilage treatment and show sustained release of a loaded drug upon degradation.

(3) Analysis on Mechanical Properties of HA-PG Hydrogel Patch

Figure 10A:
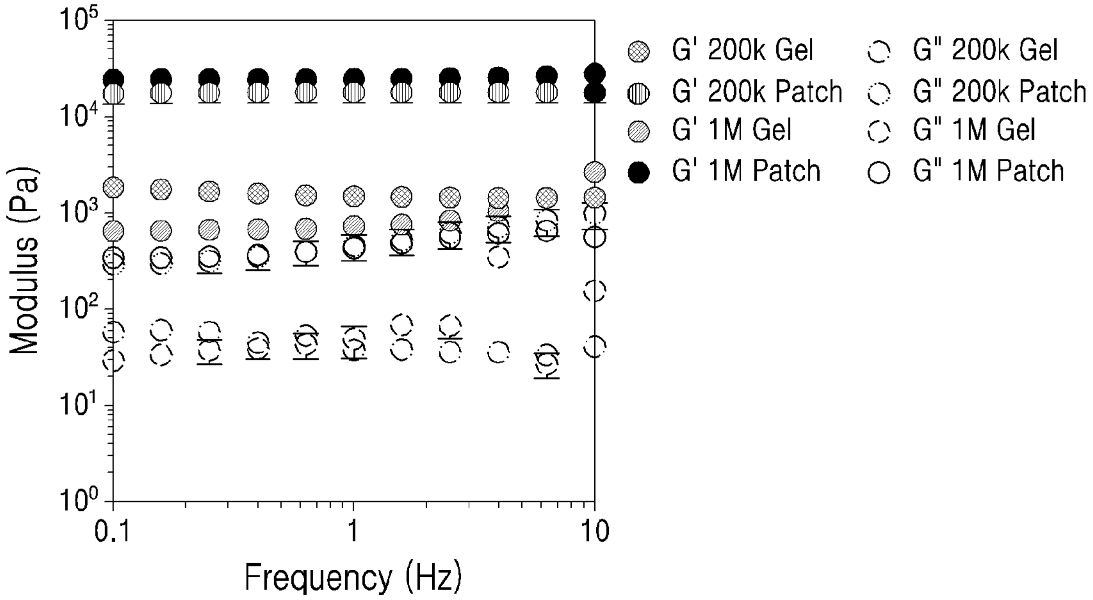
FIG. 10A shows the result of measuring a storage modulus and a loss modulus of the HA-PG hydrogel patch.

The elastic modulus of the HA-PG hydrogel patch or the HA-PG bulk hydrogel was measured at a frequency of from 0.1 Hz and 10 Hz by using a rheometer. As a result of analysis, both the HA-PG hydrogel patch (Patch) and the HA-PG bulk hydrogel (Gel) showed higher storage moduli G' than loss moduli G". Thus, it was found that the internal structure is formed of a stable polymer network (FIG. 10A).

Figure 10B:
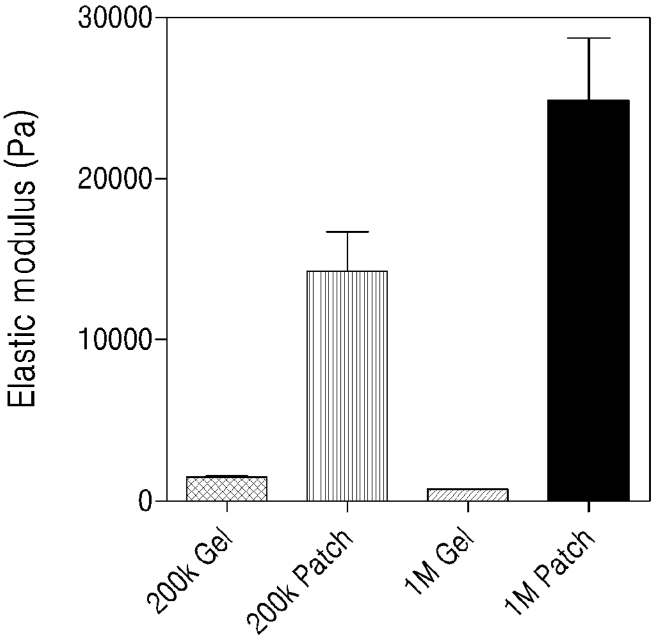
FIG. 10B shows the result of measuring an average storage modulus of the HA-PG hydrogel patch.
Figure 10C:
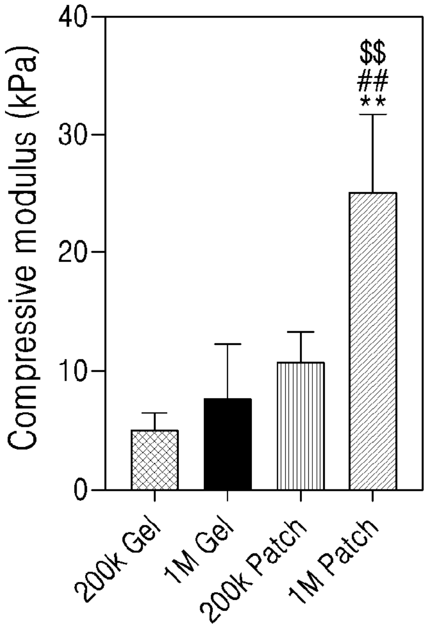
FIG. 10C shows the result of measuring the indentation strength of the HA-PG hydrogel patch.

Further, the average storage moduli G' of the HA-PG bulk hydrogels (200 kDa and 1 MDa Gels) were very low, whereas the average storage moduli G' of the HA-PG hydrogel patches (200 kDa and 1 MDa Patches) were in the range of from about 14 kPa to about 24 kPa. Thus, it was found that the average storage moduli G' increased considerably (FIG. 10B). Furthermore, when the indentation strength of HA-PG bulk hydrogels (200 kDa Gel and 1 MDa Gel) and the HA-PG hydrogel patches (200 kDa Patch and 1 MDa Patch) was measured, it was found that the indentation strength of the HA-PG hydrogel patch (1 MDa Patch) was significantly high (FIG. 10C).

Therefore, the HA-PG hydrogel patch is expected to serve as a buffer to reduce damage caused by wear of cartilage tissues in addition to its role as a drug delivery system.

Figure 11A:
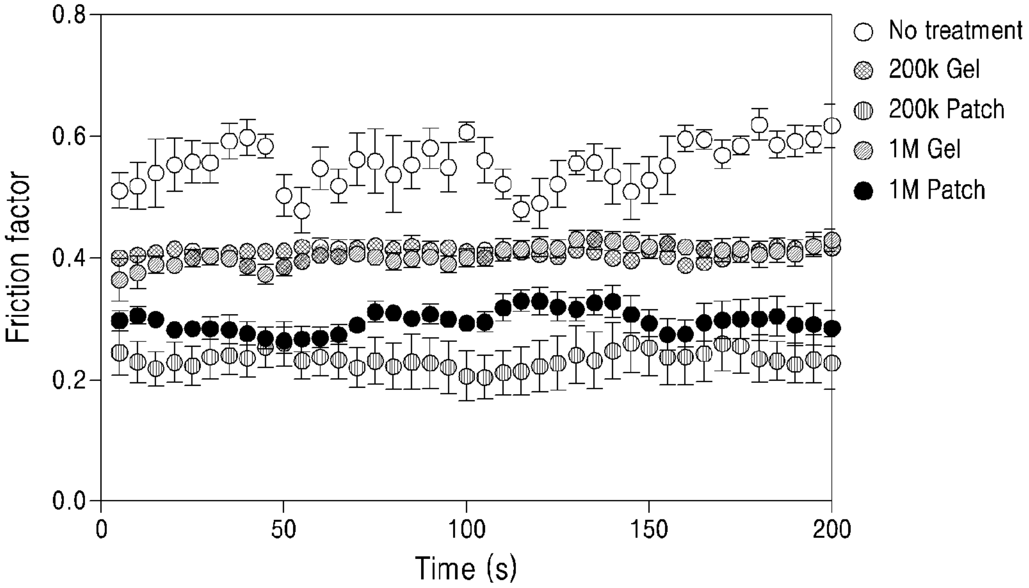
FIG. 11A shows the result of analyzing a friction factor of the HA-PG hydrogel patch.
Figure 11B:
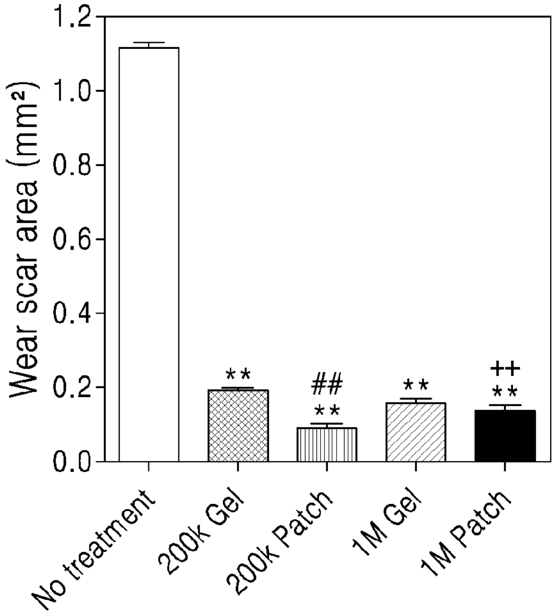
FIG. 11B shows the result of analyzing the area of wear scar of the HA-PG hydrogel patch.
Figure 11C:
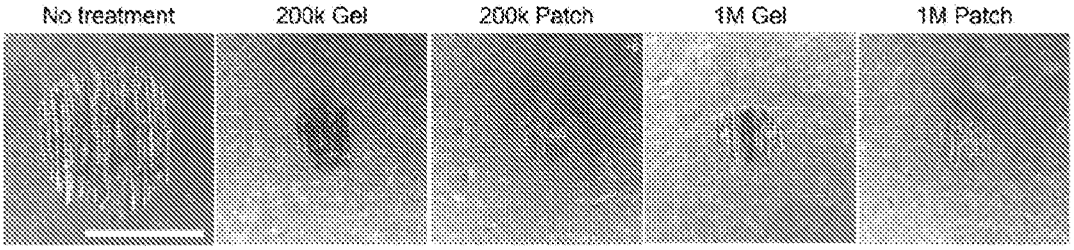
FIG. 11C shows the result of analyzing the degree of wear scar of the HA-PG hydrogel patch.

Meanwhile, a friction factor was measured by moving a friction force analyzer at a speed of 0.01 m/s in a state where a normal force of 5 N was applied between stainless steel surfaces coated with the HA-PG hydrogel patch or the HA-PG bulk hydrogel. As a result of measurement, the friction factor was the highest in the case of no coating (No treatment), followed by the HA-PG bulk hydrogels (200 kDa and 1 MDa Gels) and the HA-PG hydrogel patches (200 kDa and 1 MDa Patches) (FIG. 11A). Further, in the case of no coating (No treatment), a large wear scar was formed due to friction, and in the HA-PG bulk hydrogels (200 kDa and 1 MDa Gels) and the HA-PG hydrogel patches (200 kDa and 1 MDa Patches), a small wear scar was formed (FIG. 11B). Therefore, in the HA-PG bulk hydrogels (200 kDa and 1 MDa Gels) and the HA-PG hydrogel patches (200 kDa and 1 MDa Patches), the area of wear scar was significantly reduced compared with the case of no coating (No treatment) (FIG. 11C).

Therefore, the HA-PG hydrogel patch is expected to serve as a buffer to improve wear resistance by reducing friction between joints.

Example 2

(1) Evaluation of Sustained Drug Release Pattern of Dexamethasone-Loaded HA-PG Hydrogel Patch When an HA-PG hydrogel patch or HA-PG bulk hydrogel was prepared according to Preparation Example 2, an HA-PG solution added with dexamethasone was used (dexamethasone content per patch=0.5 mg). Then, a sustained drug release pattern was checked.

Figure 12:
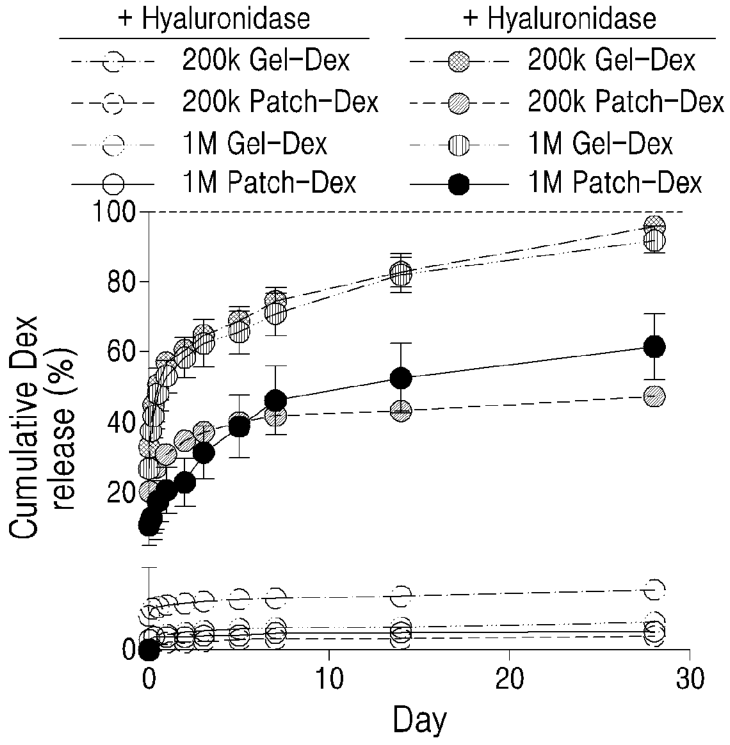
FIG. 12 shows the result of evaluating a sustained drug release pattern of a dexamethasone-loaded HA-PG hydrogel patch.

Thereafter, the HA-PG hydrogel patch or HA-PG bulk hydrogel loaded with dexamethasone was immersed in PBS at 37° C. and then treated with a hyaluronidase until degradation (20 U/sample). As a result of evaluation of the sustained drug release pattern by UV-vis analysis, release of dexamethasone hardly occurred in an environment without any degradative enzyme due to strong bonds between pyrogallol groups and various nucleophilic functional groups of proteins, but it was found that the drug was effectively released when treated with a degradative enzyme in a bio-inspired environment. In particular, a hydrogel in the form of a gel is degraded at a higher rate than a hydrogel in the form of a patch. Thus, it was confirmed that the dexamethasone-loaded HA-PG hydrogel patches (200 kDa Patch-Dex and 1 MDa Patch-Dex) can release dexamethasone in a sustained manner compared with the dexamethasone-loaded HA-PG bulk hydrogels (200 kDa Gel-Dex and 1 MDa Gel-Dex) (FIG. 12).

Therefore, when the HA-PG hydrogel patch loaded with a drug is applied to a disease site, such as an inflammation site, where the activity of a hyaluronidase is increased, it is expected to induce a sustained therapeutic effect through effective sustained drug release.

(2) Evaluation of Inflammatory Arthritis Treatment Efficacy, Ambulatory Function Improvement and Cartilage Damage Reduction/Cartilage Tissue Regeneration Promotion of Dexamethasone-Loaded HA-PG Hydrogel Patch Inflammatory arthritis was induced by cutting the anterior cruciate ligament of each mouse. The cut site was treated with a dexamethasone-loaded HA-PG hydrogel patch or HA-PG bulk hydrogel (dexamethasone content per mouse=0.5 mg).

Figure 13:
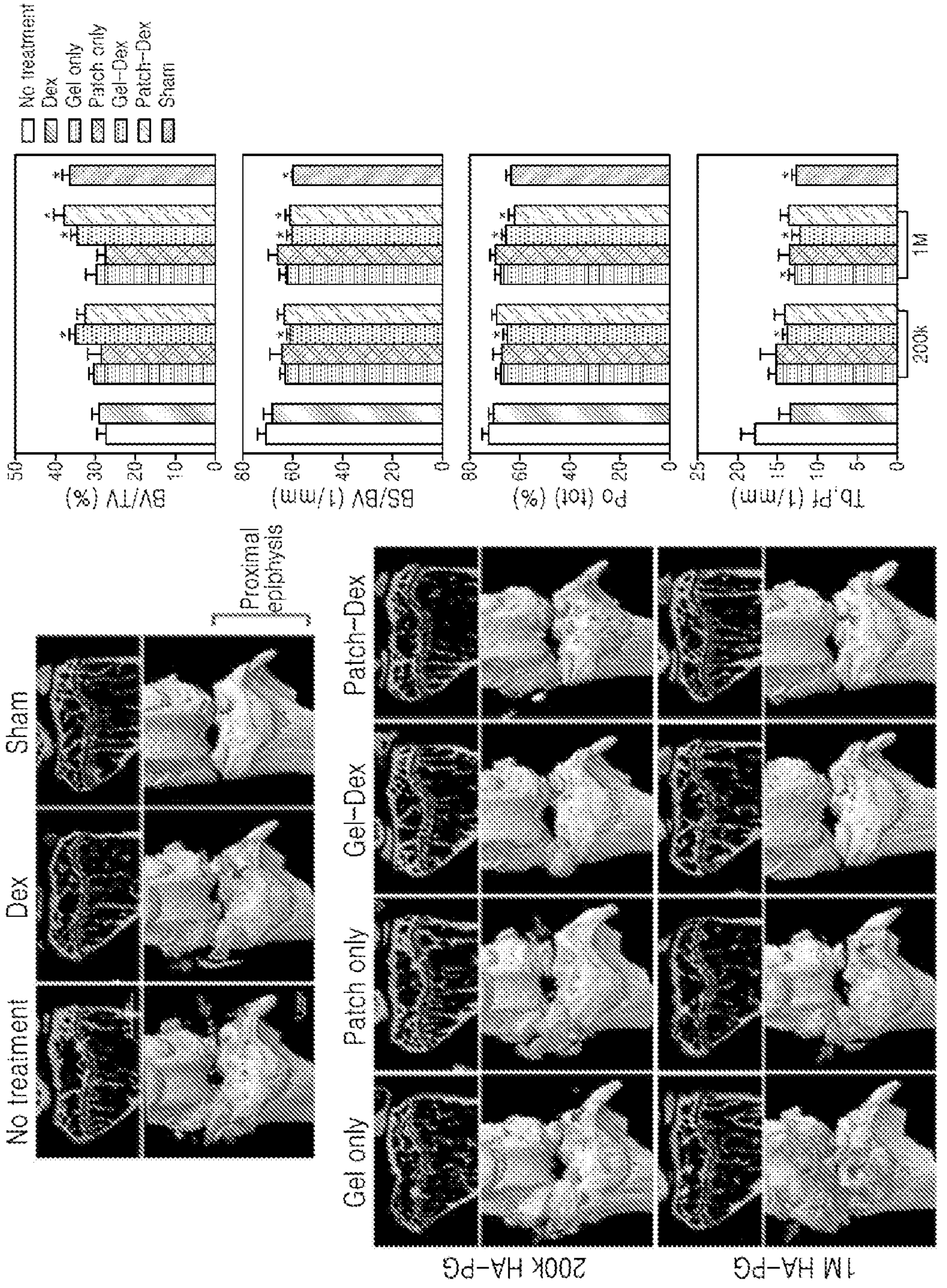
FIG. 13 shows the result of evaluating inflammatory arthritis treatment efficacy of the dexamethasone-loaded HA-PG hydrogel patch.

As a result of evaluation of the inflammatory arthritis treatment efficacy by micro-CT after 8 weeks, in the case of no treatment (No treatment), the meniscus (red arrows) was abnormally damaged and the bone volume/tissue volume (BV/TV) of the proximal epiphysis of the tibia was reduced. Also, as a porous structure of the trabecular bone collapsed (total porosity; Po(tot), yellow arrows), the bone surface/volume (BS/BV) decreased, resulting in a decrease in trabecular pattern factor (Tb.Pf). However, in the case of treatment with the dexamethasone-loaded HA-PG bulk hydrogel (200 kDa Gel-Dex) or the dexamethasone-loaded HA-PG hydrogel patch (200 kDa Patch-Dex), sustained release of dexamethasone was induced at the disease site, and, thus, the inflammation was treated and tissue regeneration was induced to the level of the normal group (Sham) (FIG. 13). Even in the case of using hyaluronic acid having a molecular weight of 1 MDa, which is widely used clinically, instead of hyaluronic acid having a molecular weight of 200 kDa, the same therapeutic efficacy was achieved.

Figure 14:
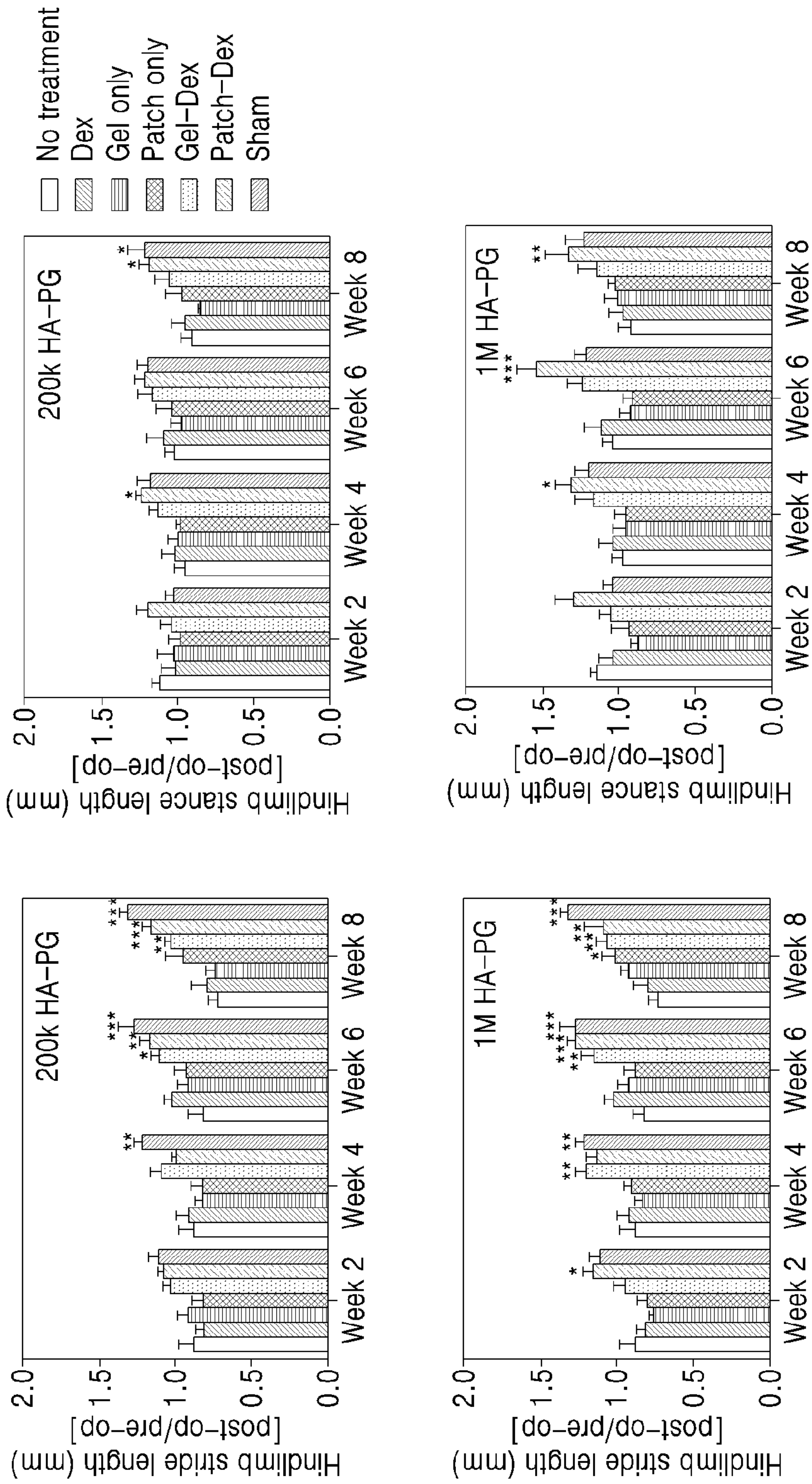
FIG. 14 shows the result of evaluating ambulatory function improvement by the dexamethasone-loaded HA-PG hydrogel patch.

Meanwhile, in order to evaluate improvement in ambulatory function, analysis on ambulatory function of the mice was performed every 2 weeks for 8 weeks. As a result of analyzing the stride length and the stance length, in the case of treatment with the dexamethasone-loaded HA-PG bulk hydrogels (200 kDa Gel-Dex and 1 MDa Gel-Dex) or the dexamethasone-loaded HA-PG hydrogel patches (200 kDa Patch-Dex and 1 MDa Patch-Dex), the ambulatory function was improved. Particularly, in the case of treatment with the dexamethasone-loaded HA-PG hydrogel patches (200 kDa Patch-Dex and 1 MDa Patch-Dex), a significant improvement in ambulatory function was induced to the level of the normal group (Sham) (FIG. 14).

Figure 15:
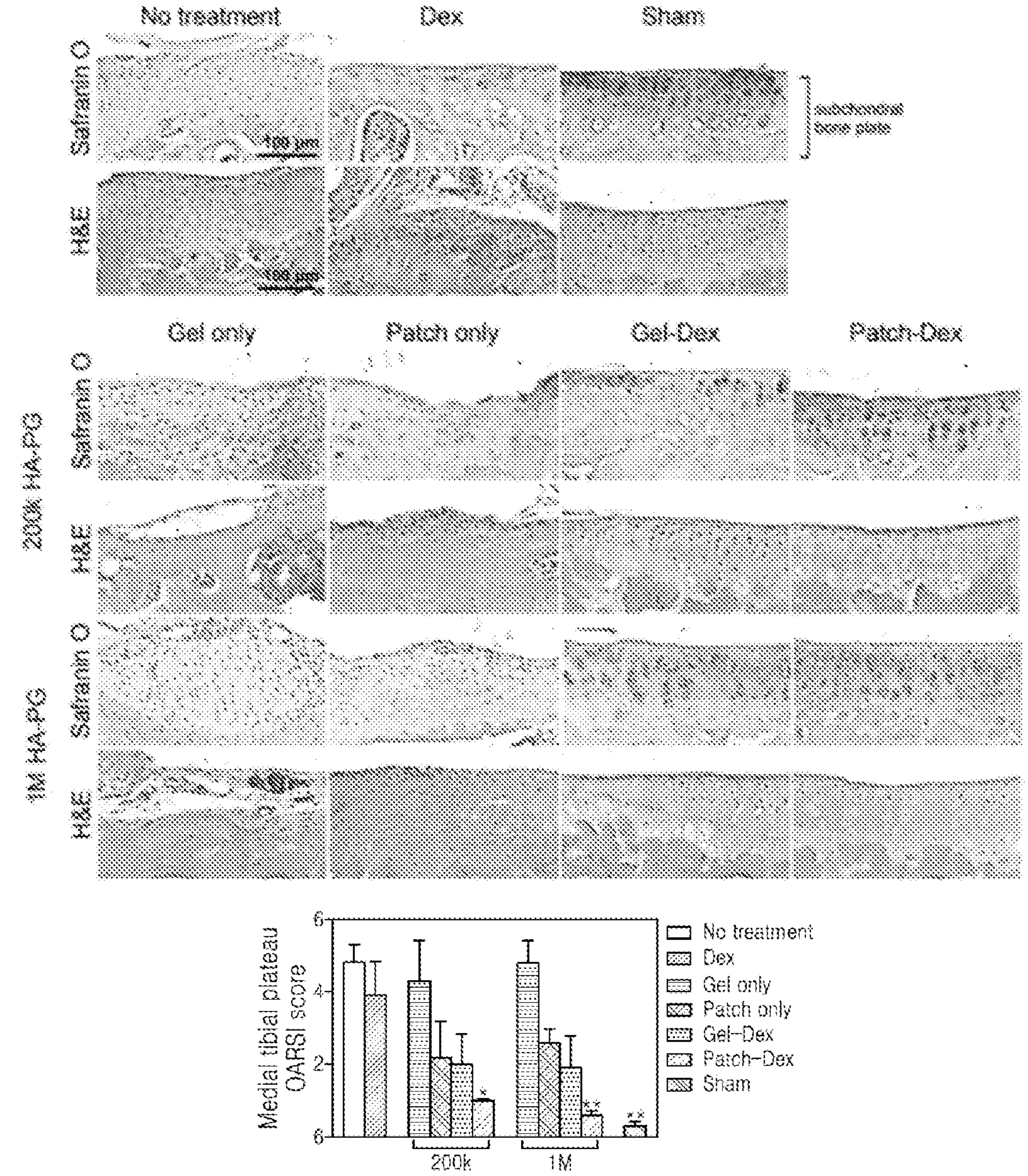
FIG. 15 shows the result of evaluating cartilage damage reduction/cartilage tissue regeneration promotion by the dexamethasone-loaded HA-PG hydrogel patch.

Meanwhile, in order to evaluate reduction in cartilage damage/promotion of cartilage tissue regeneration, histological analysis was performed after 8 weeks. Specifically, changes in the expression level of proteoglycan in the articular surface (red part in the result of Safranin O staining), changes in cell arrangement, changes in cartilage tissue, and damage patterns were analyzed by Safranin O staining and hematoxylin & eosin staining. As a result of analysis, in the case of no treatment (No treatment), the thickness of the subchondral bone plate increased abnormally, and in the case of treatment with dexamethasone (Dex), the HA-PG bulk hydrogel (Gel only) or the HA-PG hydrogel patch (Patch only), the thickness of the sublingual bone plate was partially reduced, but cartilage damage and extracellular matrix loss were not recovered (OARSI score). However, in the case of treatment with the dexamethasone-loaded HA-PG hydrogel patch (200 kDa Patch-Dex and 1 MDa Patch-Dex), the osteoarthritis treatment efficacy was greatly improved and cartilage tissue regeneration was induced to the level of the normal group (Sham) due to sustained release of dexamethasone and supply of hyaluronic acid (FIG. 15).

Preparation Example 3

(1) Fabrication of Inorganic Mineral Particle-Added HA-PG Hydrogel Patch

Figure 16A:
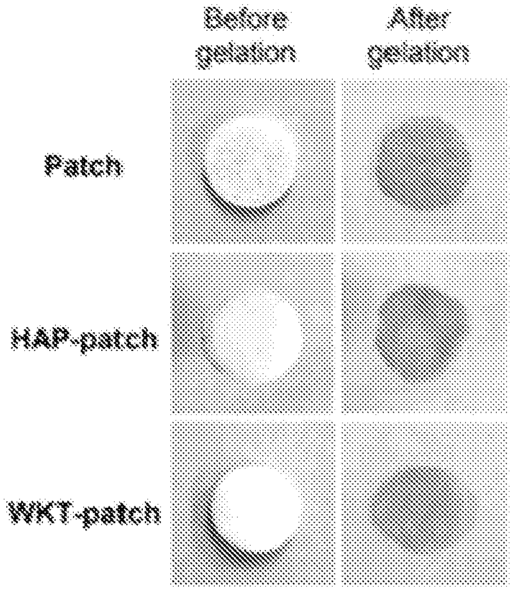
FIG. 16A shows where and how a phenol group-functionalized biocompatible polymer hydrogel patch to which inorganic mineral particles are added is applied according to an embodiment of the present disclosure.
Figure 16B:
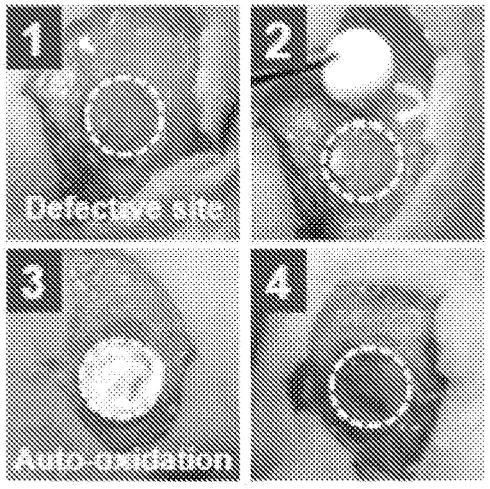
FIG. 16B shows where and how a phenol group-functionalized biocompatible polymer hydrogel patch to which inorganic mineral particles are added is applied according to an embodiment of the present disclosure.

A pyrogallol-functionalized hyaluronic acid (hereinafter, referred to as HA-PG) (molecular weight=200 kDa) was dissolved in distilled water at a concentration of 1 (w/v) % by using 5-hydroxydopamine, hydroxyapatite (HAP) or whitlockite (WKT) was added thereto at a concentration of 1 (w/v) % or 5 (w/v) %, and 80 μl of the 1 (w/v) % HA-PG solution added with HAP or WKT was poured into an 8 mm cylindrical mold and then freeze-dried overnight at −80° C. to fabricate an HAP or WKT-added HA-PG hydrogel patch (HAP-patch or WKT-patch) with a diameter of 8 mm and a thickness of 1.6 mm (FIG. 16A). The fabricated HAP or WKT-added HA-PG hydrogel patch is in a dry state and thus is easy to store. Also, it is fabricated in the form of a thin film and thus can be easily cut into a desired shape. Therefore, it is convenient to use. Also, it can be applied directly to a diseased site due to excellent tissue adhesion of the oxidized pyrogallol group (FIG. 16B).

Figure 17A:
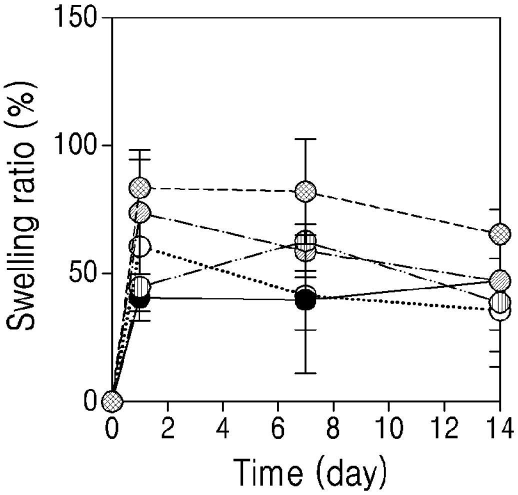
FIG. 17A shows the result of analyzing a swelling ratio of an inorganic mineral particle-added HA-PG hydrogel patch.
Figure 17B:
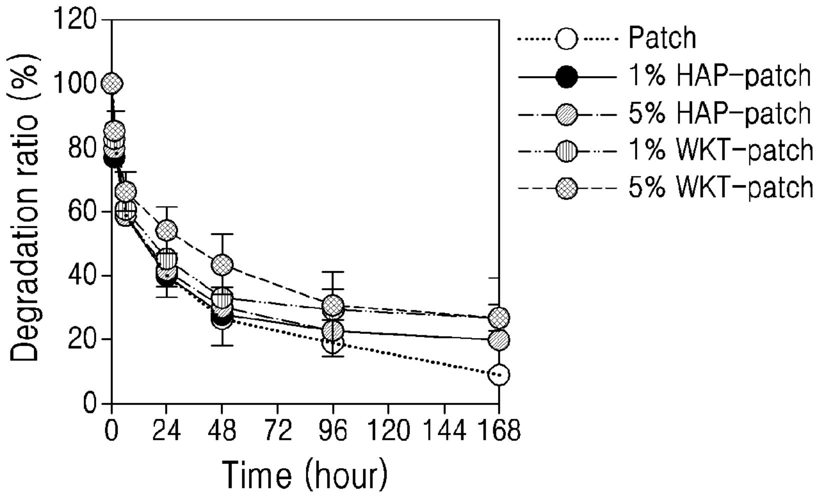
FIG. 17B shows the result of analyzing a degradation rate of the inorganic mineral particle-added HA-PG hydrogel patch by an enzyme.

(2) Analysis on Physical Properties of Inorganic Mineral Particle-Added HA-PG Hydrogel Patch The HA-PG hydrogel patch, the HAP-added HA-PG hydrogel patch or the WKT-added HA-PG hydrogel patch was immersed in PBS at 37° C. similar to in vivo conditions for 14 days, and the swelling ratio was measured after 12 hours, 7 days and 14 days. As a result of measurement, the swelling ratio of the HA-PG hydrogel patch (5% WKT-patch) added with WKT at a concentration of 5 (w/v) % was higher than those of the other groups (FIG. 17A). It can be seen that under high concentration conditions where interactions between inorganic ions and oxidized pyrogallol groups are important, the electrolyte of PBS weakens such interactions, which results in an increase in swelling ratio.

Since various degradative enzymes exist in the actual in vivo environment, the HA-PG hydrogel patch, the HAP-added HA-PG hydrogel patch or the WKT-added HA-PG hydrogel patch was immersed in PBS at 37° C. and then treated with a hyaluronidase until degradation (300 U/sample). The weight of the HA-PG hydrogel patch, the HAP-added HA-PG hydrogel patch or the WKT-added HA-PG hydrogel patch was measured at regular time intervals to measure the degrees of degradation over time. As a result of measurement, the degradation rates of the WKT-added HA-PG hydrogel patches (1% WKT-Patch and 5% WKT-Patch) by the enzyme decreased considerably due to interactions between the inorganic ions and the pyrogallol groups as well as cross-linking between the pyrogallol groups. (FIG. 17C).

Figure 18:
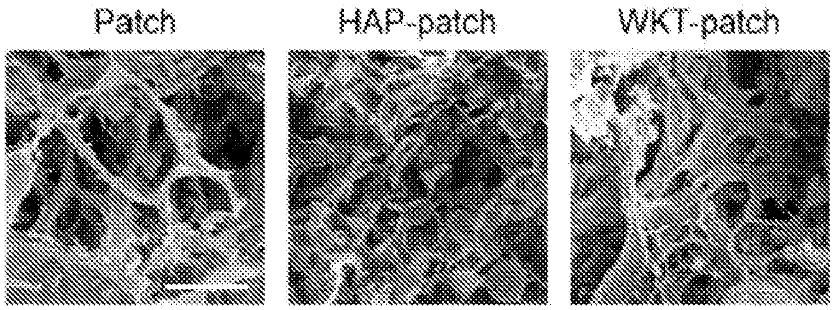
FIG. 18 shows the results of checking the internal structure of the inorganic mineral particle-added HA-PG hydrogel patch.

(3) Analysis on Internal Structure of Inorganic Mineral Particle-Added HA-PG Hydrogel Patch As a result of analyzing the internal structure of the HA-PG hydrogel patch, the HAP-added HA-PG hydrogel patch or the WKT-added HA-PG hydrogel patch by scanning electron microscopy (SEM) analysis, it was found that all the patches have a porous structure with microporosity. In particular, in the case of the HAP-added HA-PG hydrogel patch (HAP-patch) and the WKT-added HA-PG hydrogel patch (WKT-patch), a dense internal structure is formed due to interactions between the inorganic ions and the oxidized pyrogallol groups (FIG. 18).

Figure 19:
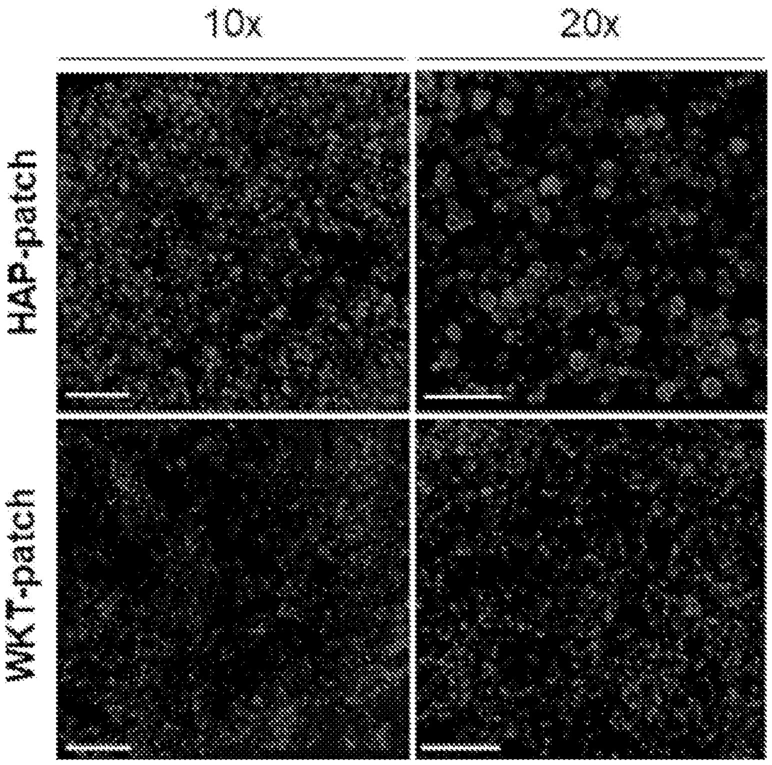
FIG. 19 shows the distribution of inorganic mineral particles in the inorganic mineral particle-added HA-PG hydrogel patch.

(4) Distribution of Inorganic Mineral Particles in Inorganic Mineral Particle-Added HA-PG Hydrogel Patch Alexa Fluor 594, a fluorescent substance, was chemically conjugated to HAP or WKT and then added to the HA-PG hydrogel patch to fabricate an HAP-added HA-PG hydrogel patch labelled with a fluorescent substance or a WKT-added HA-PG hydrogel patch labelled with a fluorescent substance, and the distribution of inorganic mineral particles was observed with a confocal microscope. As a result of observation, it was confirmed that the inorganic mineral particles were evenly distributed in all the patches (FIG. 19).

Figure 20A:
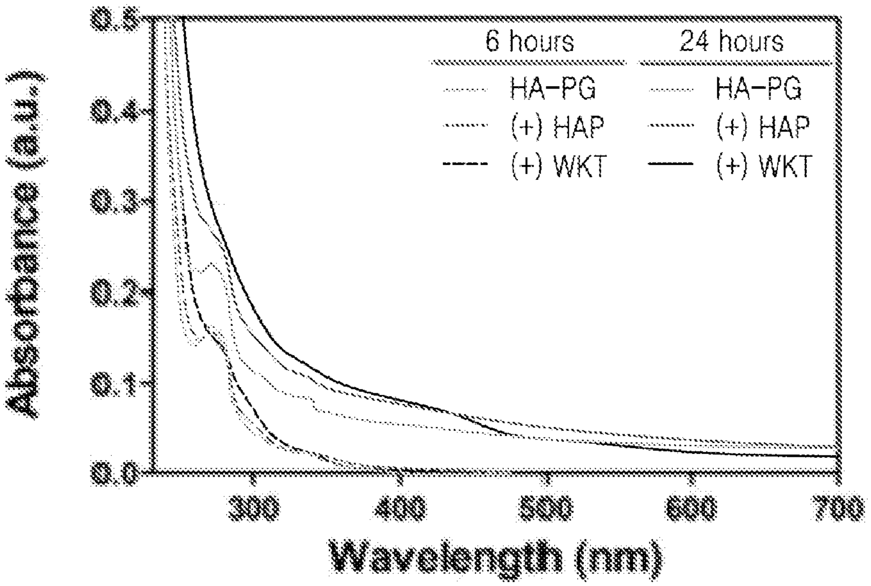
FIG. 20A shows the result of analyzing a cross-linking mechanism of the inorganic mineral particle-added HA-PG hydrogel patch.

(5) Analysis on Cross-Linking Mechanism of Inorganic Mineral Particle-Added HA-PG Hydrogel Patch Inorganic mineral particles, HAP or WKT, were mixed into an HA-PG solution and allowed reaction for 6 hours or 24 hours and then, chemical reactions between inorganic ions (Ca, Mg, P) released from the inorganic mineral particles and oxidized pyrogallol groups were analyzed by UV-vis spectrophotometry. It is observed that the 280 nm peak shifts to shorter wavelengths with an increase in the reaction time after mixing of HAP or WKT (FIG. 20A).

Figure 20B:
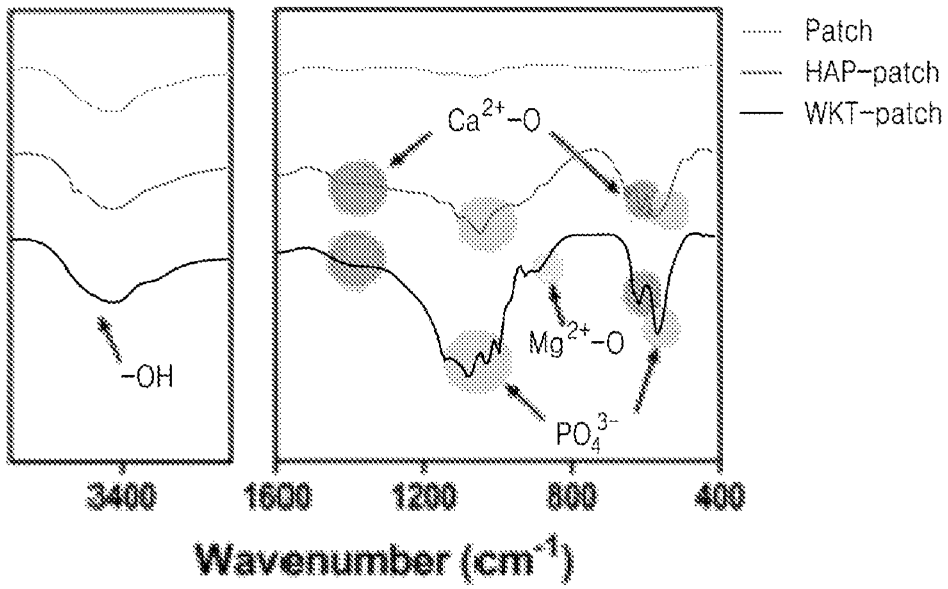
FIG. 20B shows the result of analyzing a cross-linking mechanism of the inorganic mineral particle-added HA-PG hydrogel patch.

The chemical structure of the HA-PG hydrogel patch, the HAP-added HA-PG hydrogel patch or the WKT-added HA-PG hydrogel patch was analyzed by Fourier-transform infrared spectroscopy (FT-IR) analysis. The 3400 $cm^{-1}$ peak representing —OH group was observed in all the patches, and the 471 $cm^{-1}$ peak and peak in the 1000 to 1100 $cm^{-1}$ region representing $PO_4^{3-}$ group increased in HAP-added HA-PG hydrogel patch (HAP-patch) and WKT-added HA-PG hydrogel patch (WKT-patch). Also, the $Ca^{2+}$—O peaks were observed in both the HAP-added HA-PG hydrogel patch (HAP-patch) and the WKT-added HA-PG hydrogel patch (WKT-patch), and the $Mg^{2+}$—O peak was observed only in the WKT-added HA-PG hydrogel patch (WKT-patch) (FIG. 20B).

Figure 20C:
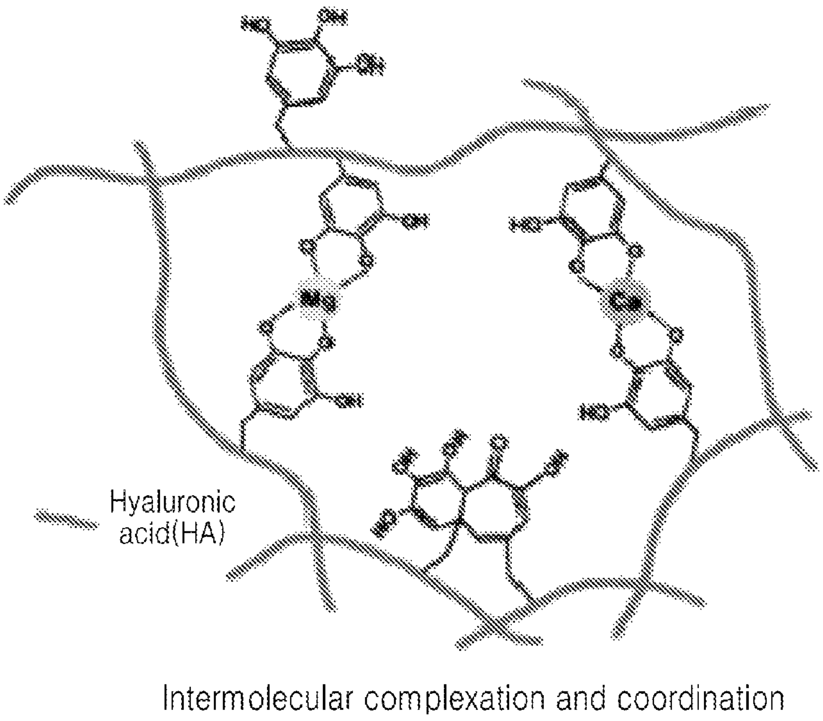
FIG. 20C shows the result of analyzing a cross-linking mechanism of the inorganic mineral particle-added HA-PG hydrogel patch.

Therefore, the inorganic mineral particle-added HA-PG hydrogel patch is expected to further increase the mechanical strength via the interactions between the inorganic ions released from the inorganic mineral particles and the oxidized pyrogallol groups (i.e., the formation of a complex compound through coordination bonding) as well as cross-linking between the oxidized pyrogallol groups and thus to enhance the bone regeneration efficacy (FIG. 20C).

Figure 21A:
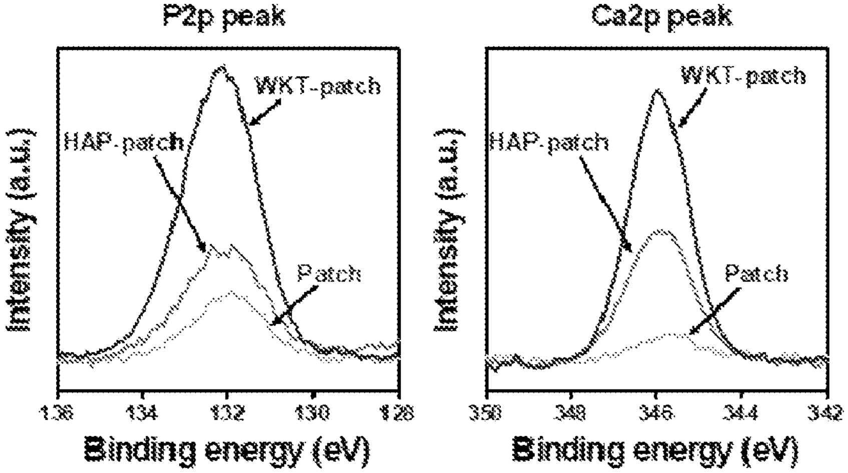
FIG. 21A shows the result of analyzing the chemical composition of the inorganic mineral particle-added HA-PG hydrogel patch.
Figures 21B, 22A:
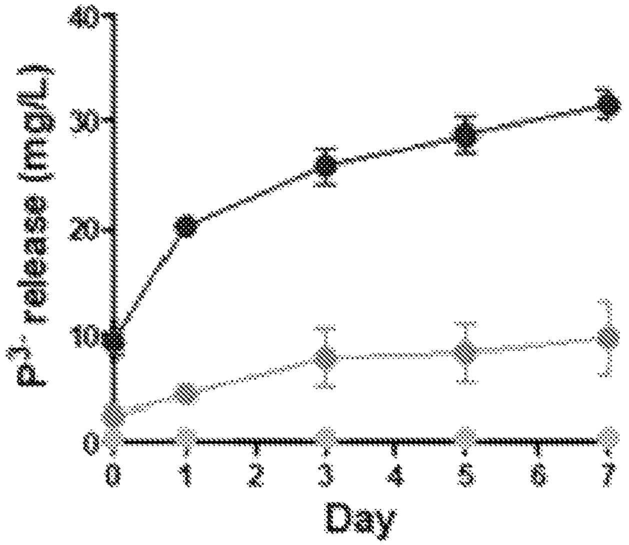
FIG. 21B shows the result of analyzing the chemical composition of the inorganic mineral particle-added HA-PG hydrogel patch.
FIG. 22A shows the result of evaluating an inorganic ion release pattern of the inorganic mineral particle-added HA-PG hydrogel patch.

(6) Chemical Composition Analysis on Inorganic Mineral Particle-Added HA-PG Hydrogel Patch The chemical composition of the HA-PG hydrogel patch, the HAP-added HA-PG hydrogel patch or the WKT-added HA-PG hydrogel patch was analyzed by X-ray photoelectron spectroscopy (XPS) analysis. It is observed that the P peak and Ca peak increase in the WKT-added HA-PG hydrogel patch (WKT-patch) (FIG. 21A). As a result of measurement of the amounts of Ca, P and Mg, which are inorganic ions that can promote the mineralization of bone tissue, Ca and P elements increased in the HAP-added HA-PG hydrogel patch (HAP-patch) and the WKT-added HA-PG hydrogel patch (WKT-patch), and Mg element increased only in the WKT-added HA-PG hydrogel patch (WKT-patch) (FIG. 21B).

Since the inorganic mineral particle-added HA-PG hydrogel patch is loaded with inorganic ions that can promote bone regeneration, it is expected to enhance the bone regeneration efficacy.

Figure 22B:
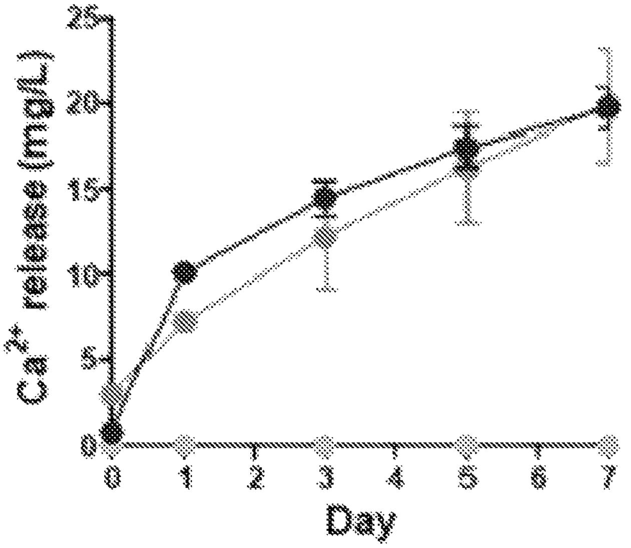
FIG. 22B shows the result of evaluating an inorganic ion release pattern of the inorganic mineral particle-added HA-PG hydrogel patch.
Figure 22C:
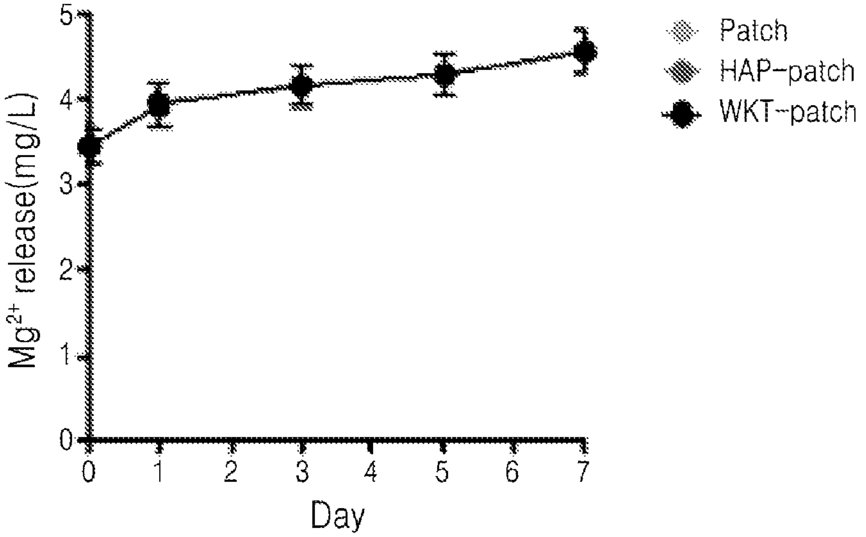
FIG. 22C shows the result of evaluating an inorganic ion release pattern of the inorganic mineral particle-added HA-PG hydrogel patch.

(7) Evaluation of Inorganic Ion Release Pattern of Inorganic Mineral Particle-Added HA-PG Hydrogel Patch Inorganic ion release patterns of the HA-PG hydrogel patch, the HAP-added HA-PG hydrogel patch or the WKT-added HA-PG hydrogel patch in a Tris-HCl buffer solution were analyzed by inductively coupled plasma emission spectroscopy (ICP-AES). As a result of analysis, $P^{3-}$ and $Ca^{2+}$ ions present in the inorganic mineral ions were observed to be continuously released from the HAP-added HA-PG hydrogel patch (HAP-patch) and the WKT-added HA-PG hydrogel patch (WKT-patch) (FIGS. 22A and 22B). HAP does not contain $Mg^{2+}$, but only WKT contains $Mg^{2+}$. Accordingly, it is confirmed that $Mg^{2+}$ is released only from the WKT-added HA-PG hydrogel patch (WKT-patch) (FIG. 22C). Meanwhile, it is confirmed that the HA-PG hydrogel patch releases almost no inorganic ions.

Since the HAP-added HA-PG hydrogel patch (HAP-patch) and the WKT-added HA-PG hydrogel patch (WKT-patch) can continuously release inorganic ions that help bone regeneration, they are expected to enhance the bone regeneration efficacy.

Figure 23A:
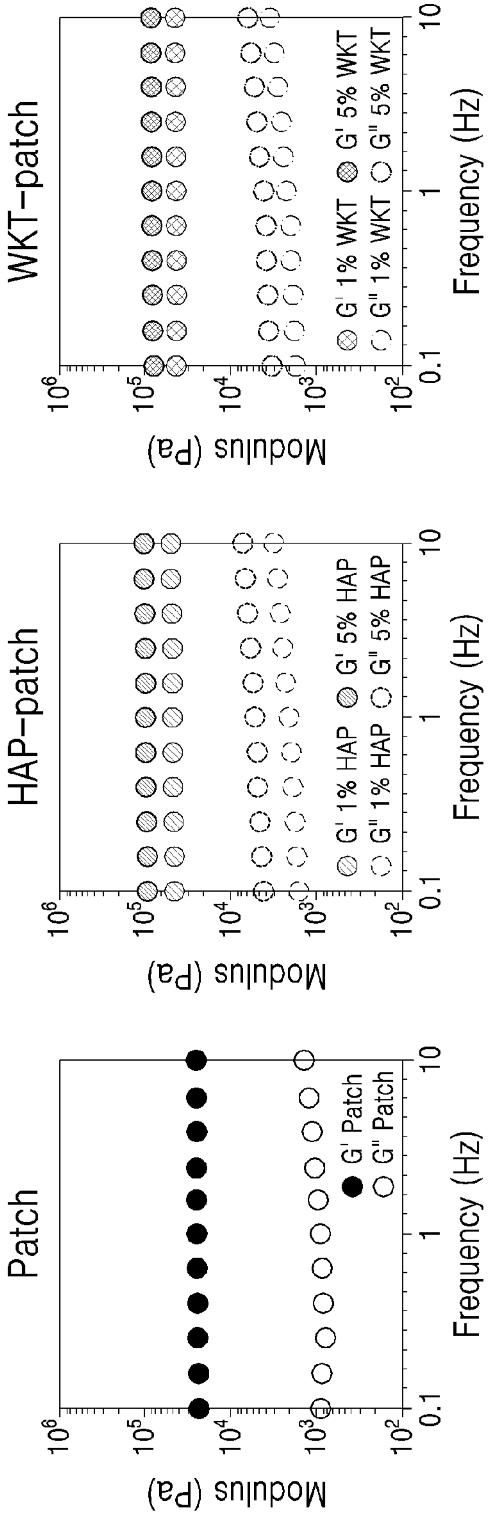
FIG. 23A shows the result of analyzing a storage modulus and a loss modulus of the inorganic mineral particle-added HA-PG hydrogel patch.

(8) Analysis on Mechanical Properties of Inorganic Mineral Particle-Added HA-PG Hydrogel Patch The elastic modulus of the HA-PG hydrogel patch, the HAP-added HA-PG hydrogel patch or the WKT-added HA-PG hydrogel patch was measured at a frequency of from 0.1 Hz and 10 Hz by using a rheometer. As a result of analysis, all the HA-PG hydrogel patch, the HAP-added HA-PG hydrogel patch and the WKT-added HA-PG hydrogel patch showed higher storage moduli G' than loss moduli G". Thus, it was found that the internal structure is formed of a stable polymer network (FIG. 23A).

Figure 23B:
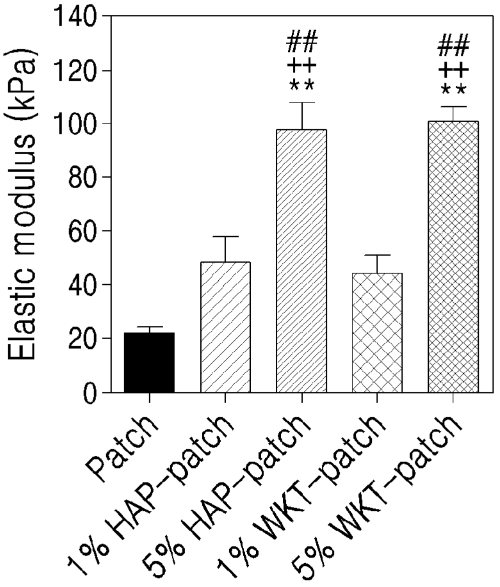
FIG. 23B shows the result of analyzing an average storage modulus of the inorganic mineral particle-added HA-PG hydrogel patch.

Further, the average storage modulus G' of the HA-PG hydrogel patch added with HAP or WKT at a concentration of 1 (w/v) % (1% HAP-patch or 1% WKT-patch) was in the range of from about 40 kPa to about 50 kPa, and the average storage modulus G' of the HA-PG hydrogel patch added with HAP or WKT at a concentration of 5 (w/v) % (5% HAP-patch or 5% WKT-patch) was about 100 kPa. Thus, it was found that the average storage moduli G' thereof were considerably increased compared with that of the HA-PG hydrogel patch (Patch) (FIG. 23B).

Therefore, the inorganic mineral particle-added HA-PG hydrogel patch is expected to promote bone generation at a bone defect site requiring mechanical strength based on the improved average elastic modulus.

Figure 24A:
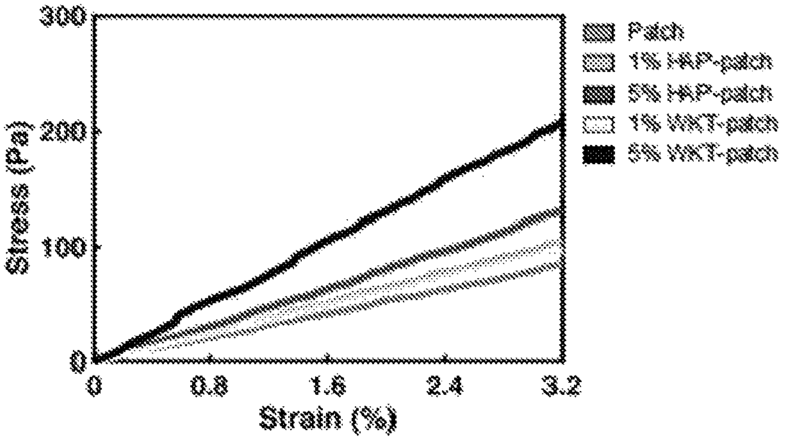
FIG. 24A shows the result of measuring the indentation strength of the inorganic mineral particle-added HA-PG hydrogel patch.
Figure 24B:
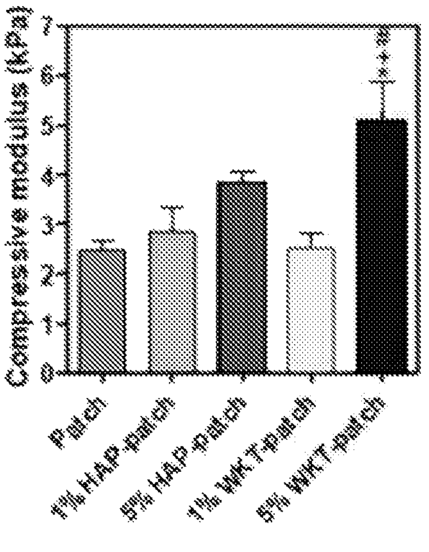
FIG. 24B shows the result of measuring the indentation strength of the inorganic mineral particle-added HA-PG hydrogel patch.

Meanwhile, the stress-strain of the HA-PG hydrogel patch, the HAP-added HA-PG hydrogel patch or the WKT-added HA-PG hydrogel patch was analyzed using an indentation analyzer, and the indentation strength was checked from the stress-strain curve (FIG. 24A). The average indentation strength of the HA-PG hydrogel patch (HA-PG patch) was about 2.5 kPa, whereas the average indentation strength of the HA-PG hydrogel patch added with HAP or WKT at a concentration of 1 (w/v) % (1% HAP-patch or 1% WKT-patch) was in the range of from about 2.5 kPa to about 3 kPa and the average indentation strength of the HA-PG hydrogel patch added with HAP or WKT at a concentration of 5 (w/v) % (5% HAP-patch or 5% WKT-patch) was in the range of from about 4 kPa to about 5 kPa (FIG. 24B). That is, it can be seen that the indentation strength increases in proportion to the concentration of inorganic mineral particles added.

Therefore, the inorganic mineral particle-added HA-PG hydrogel patch is expected to promote bone generation at a bone defect site requiring mechanical strength based on the improved indentation strength.

Figure 25A:
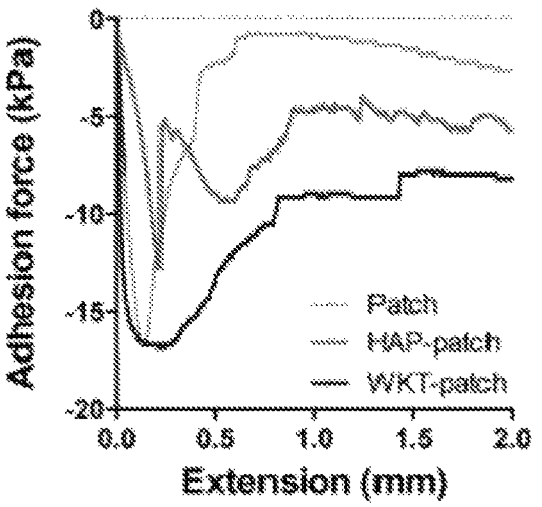
FIG. 25A shows the result of measuring a tissue adhesion of the inorganic mineral particle-added HA-PG hydrogel patch.
Figure 25B:
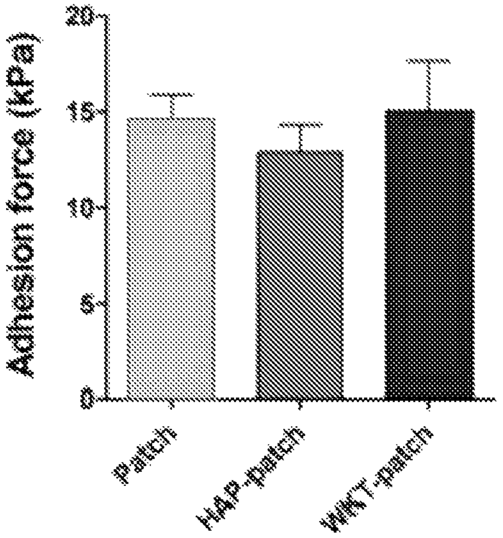
FIG. 25B shows the result of measuring a tissue adhesion of the inorganic mineral particle-added HA-PG hydrogel patch.
Figure 25C:
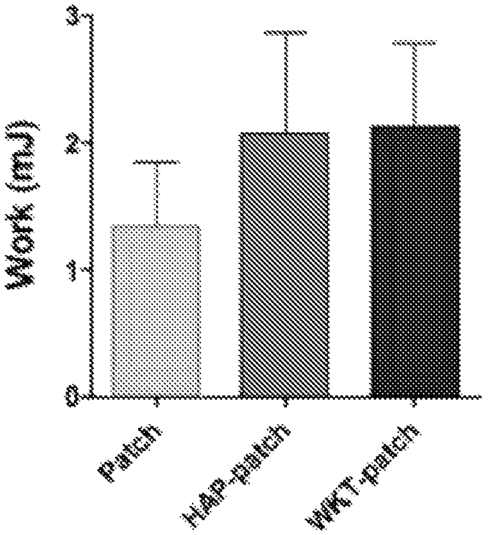
FIG. 25C shows the result of measuring a tissue adhesion of the inorganic mineral particle-added HA-PG hydrogel patch.

(9) Measurement of Tissue Adhesion of Inorganic Mineral Particle-Added HA-PG Hydrogel Patch The HA-PG hydrogel patch, the HAP-added HAPG hydrogel patch or the WKT-added HA-PG hydrogel patch was attached to the subcutaneous tissue of the back of each mouse, cross-linked through natural oxidation, and extracted together with adjacent skin tissue to perform a tack test (FIG. 25A). It was confirmed that all the patches had similar tissue adhesion at a level of from about 13 kPa to about 15 kPa (FIG. 25B). The HAP-added HA-PG hydrogel patch (HAP-patch) and the WKT-added HA-PG hydrogel patch (WKT-patch) were measured to require energy to be detached from the mouse skin tissue at a similar level to the HA-PG hydrogel patch (Patch). Accordingly, it can be seen that even when inorganic mineral particles are added, the tissue adhesion of the HA-PG hydrogel patch is maintained as it is (FIG. 25C).

Figure 26A:
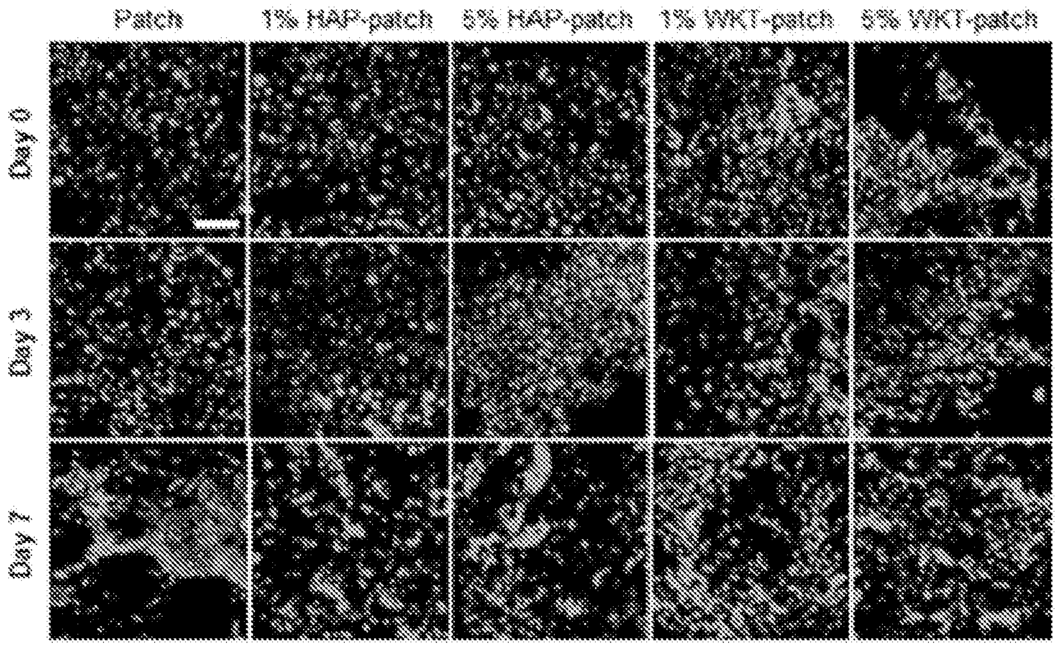
FIG. 26A shows the result of evaluating a biocompatibility of the inorganic mineral particle-added HA-PG hydrogel patch.
Figure 26B:
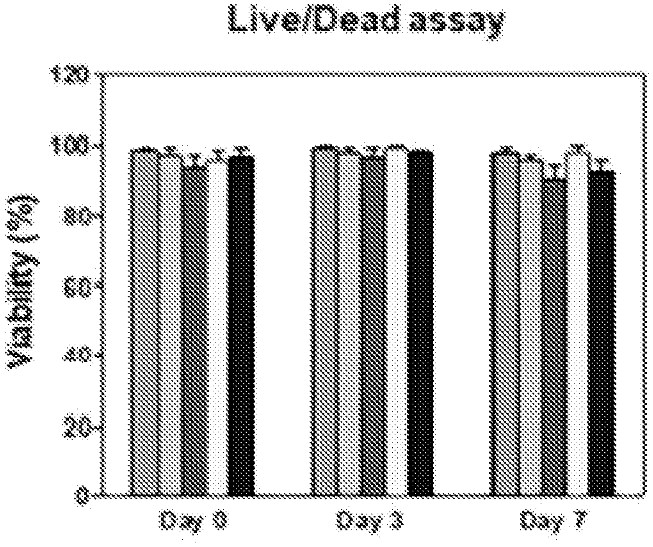
FIG. 26B shows the result of evaluating a biocompatibility of the inorganic mineral particle-added HA-PG hydrogel patch.
Figure 26C:
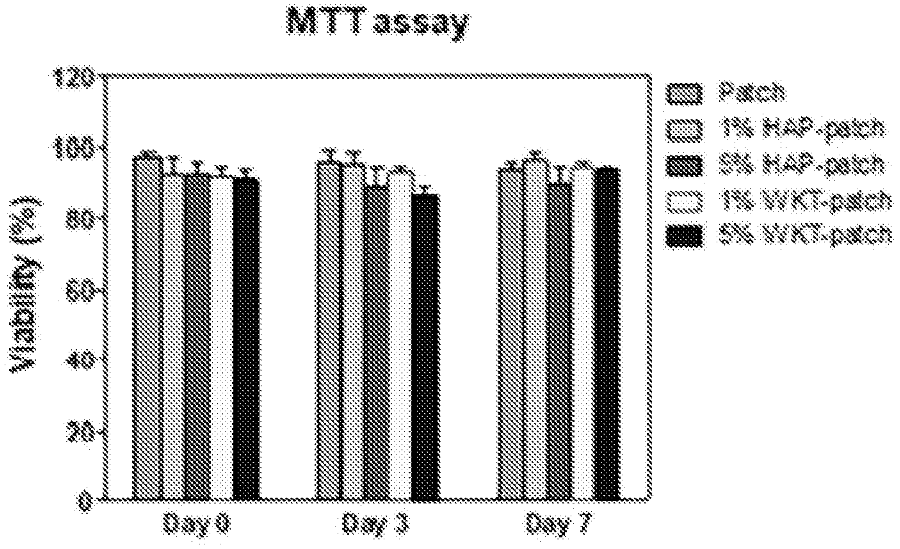
FIG. 26C shows the result of evaluating a biocompatibility of the inorganic mineral particle-added HA-PG hydrogel patch.

(10) Evaluation of Biocompatibility of Inorganic Mineral Particle-Added HA-PG Hydrogel Patch The HA-PG hydrogel patch, the HAP-added HA-PG hydrogel patch or the WKT-added HA-PG hydrogel patch was placed on the bottom of a 6-well cell culture plate, and human adipose-derived stem cells (hADSCs) were seeded and cross-linked by applying a 4.5 mg/ml sodium periodate solution, followed by three-dimensional incubation for 7 days. The cell viability was checked by Live/Dead assay and MTT assay according to the manufacturer's protocol on days 0, 3 and 7 of incubation. As a result of checking, high viability of the stem cells was observed throughout the incubation period regardless of addition of inorganic mineral particles. Thus, it can be seen that all the patches have no cytotoxicity and have excellent biocompatibility (FIGS. 26A, 26B and 26C).

Example 3

(1) Evaluation of Sustained Release Pattern of Inorganic Mineral Particle-Added HA-PG Hydrogel Patch Loaded with BMP-2

When an HA-PG hydrogel patch, an HAP-added HA-PG hydrogel patch or a WKT-added HA-PG hydrogel patch was prepared according to Preparation Example 3, an HA-PG solution added with BMP-2 was used (BMP-2 content per patch=0.5 μg). Then, a sustained drug release pattern was checked.

Figure 27A:
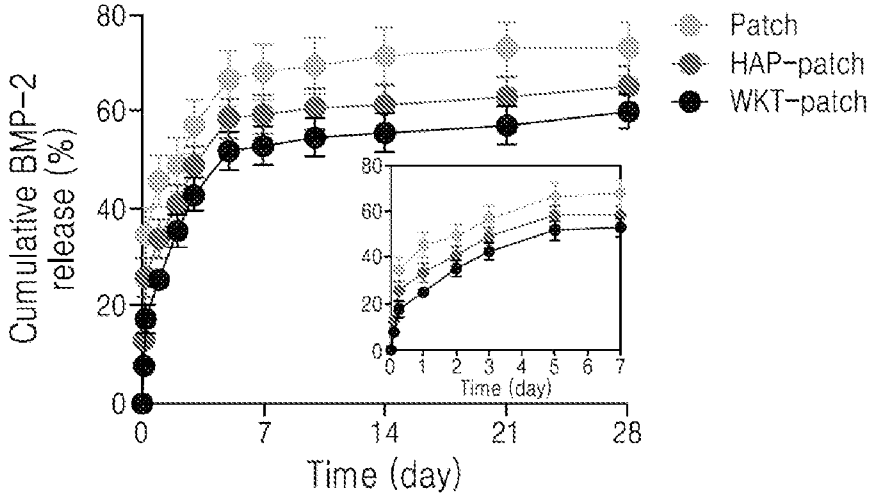
FIG. 27A shows the result of evaluating a sustained drug release pattern of an inorganic mineral particle-added HA-PG hydrogel patch loaded with BMP-2.

Thereafter, the HA-PG hydrogel patch loaded with BMP-2, the HAP-added HA-PG hydrogel patch loaded with BMP-2 or the WKT-added HA-PG hydrogel patch loaded with BMP-2 was immersed in PBS at 37° C. and then treated with a hyaluronidase until degradation (40 U/sample). As a result of evaluation of the sustained drug release pattern by UV-vis analysis, it was confirmed that the HAP-added HA-PG hydrogel patch loaded with BMP-2 (HAP-patch) or the WKT-added HA-PG hydrogel patch loaded with BMP-2 (WKT-patch) can release BMP-2 in a sustained manner compared with the BMP-2-loaded HA-PG hydrogel patch (Patch) (FIG. 27A). Therefore, they are expected to induce a sustained therapeutic effect through effective sustained drug release.

Figure 27B:
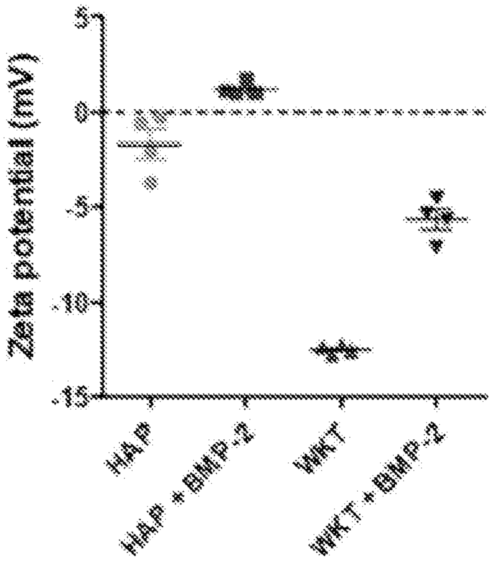
FIG. 27B shows the result of checking ionic interactions between inorganic mineral particles and BMP-2.
Figure 27C:
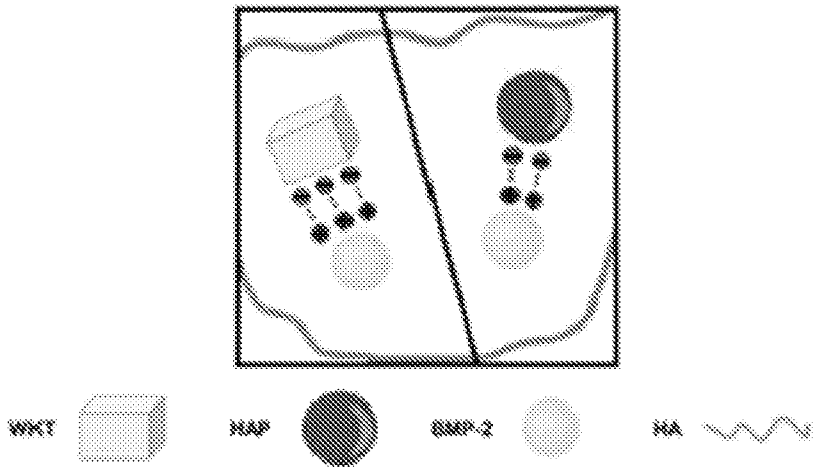
FIG. 27C shows various interactions among inorganic mineral particles, BMP-2, and phenol groups.
Figure 27D:
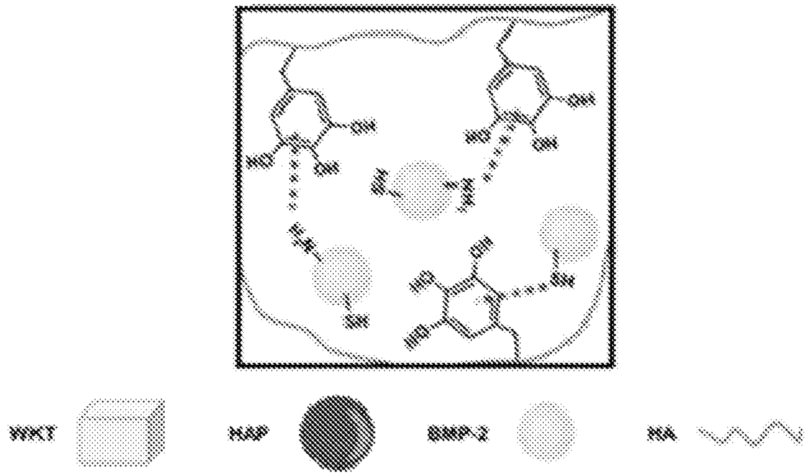
FIG. 27D shows various interactions among inorganic mineral particles, BMP-2, and phenol groups.

To elucidate this mechanism, changes in zeta potential were measured when HAP or WKT was mixed with BMP-2. As a result of measurement, ionic interactions between HAP or WKT and BMP-2 were confirmed (FIG. 27B). It is considered that release of BMP-2 can be sustained longer due to strong bonds between oxidized pyrogallol groups and various nucleophilic functional groups of BMP-2 as well as the ionic interactions between cationic BMP-2 and HAP or WKT having an anionic surface (FIGS. 27C-27D).

Since the inorganic mineral particle-added HA-PG hydrogel patch shows an improved sustained drug release pattern at a disease site, such as a bone defect site, where the activity of a hyaluronidase is increased, it is expected to exhibit an enhanced regeneration efficacy through effective delivery of a drug (particularly, bone morphogenetic protein).

(2) Verification of Bone Differentiation Promoting Effect of Inorganic Mineral Particle-Added HA-PG Hydrogel Patch Loaded with BMP-2

While human adipose-derived stem cells (hADSCs) were incubated for 21 days in the HA-PG hydrogel patch, the HAP-added HA-PG hydrogel patch, the WKT-added HA-PG hydrogel patch, the HA-PG hydrogel patch loaded with BMP-2, the HAP-added HA-PG hydrogel patch loaded with BMP-2 or the WKT-added HA-PG hydrogel patch loaded with BMP-2 under the culture medium conditions for inducing bone differentiation, the differentiation efficiency was checked.

Figure 28:
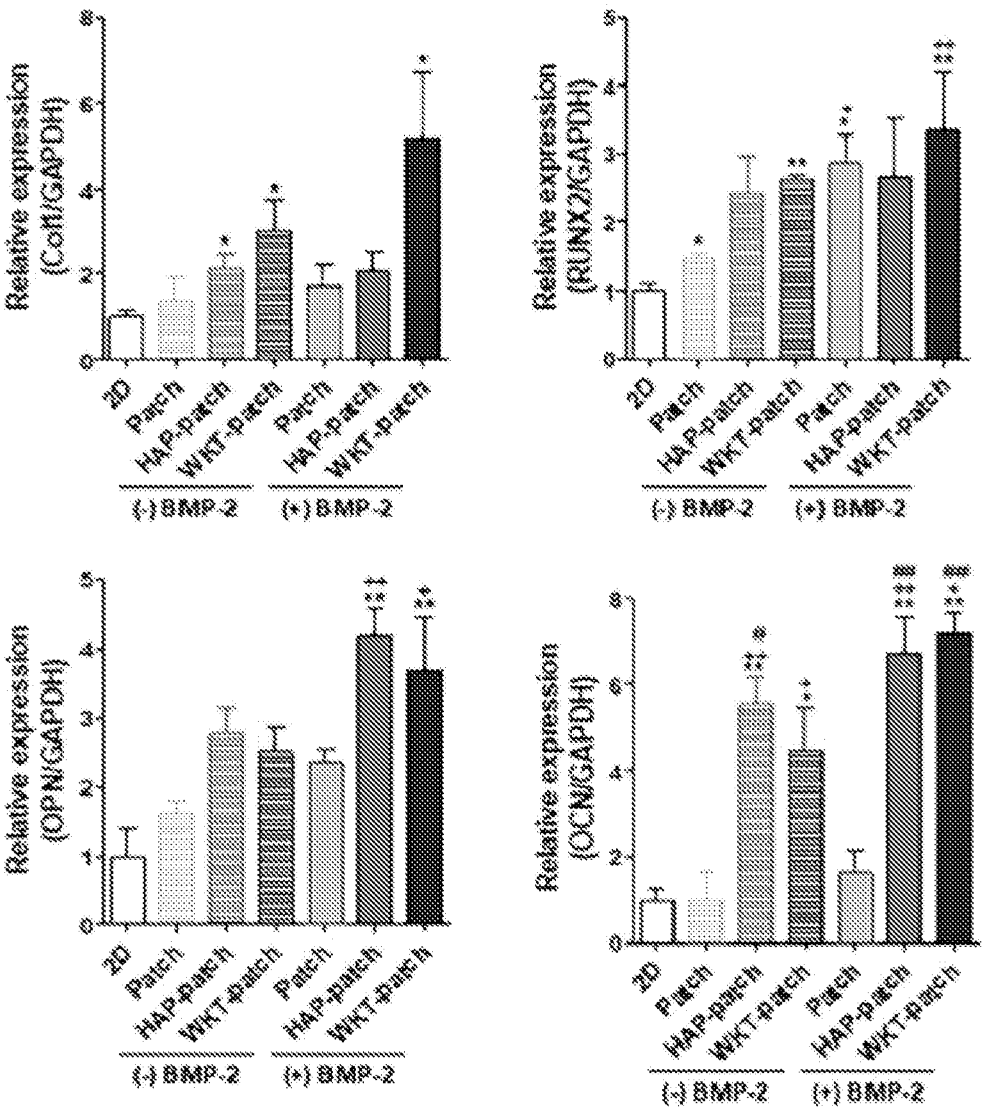
FIG. 28 shows the results of verifying bone differentiation promoting effect of the inorganic mineral particle-added HA-PG hydrogel patch loaded with BMP-2.

It is confirmed by qPCR analysis that the expression levels of bone differentiation markers collagen type 1 (Col1), runt-related transcription factor 2 (RUNX2), osteopontin (OPN) and osteocalcin (OCN) increase in the HAP- or WKT-added HA-PG hydrogel patch. In particular, it is confirmed that the expression levels of the bone differentiation markers further increase in the case where BMP-2 is loaded (FIG. 28).

Figure 29A:
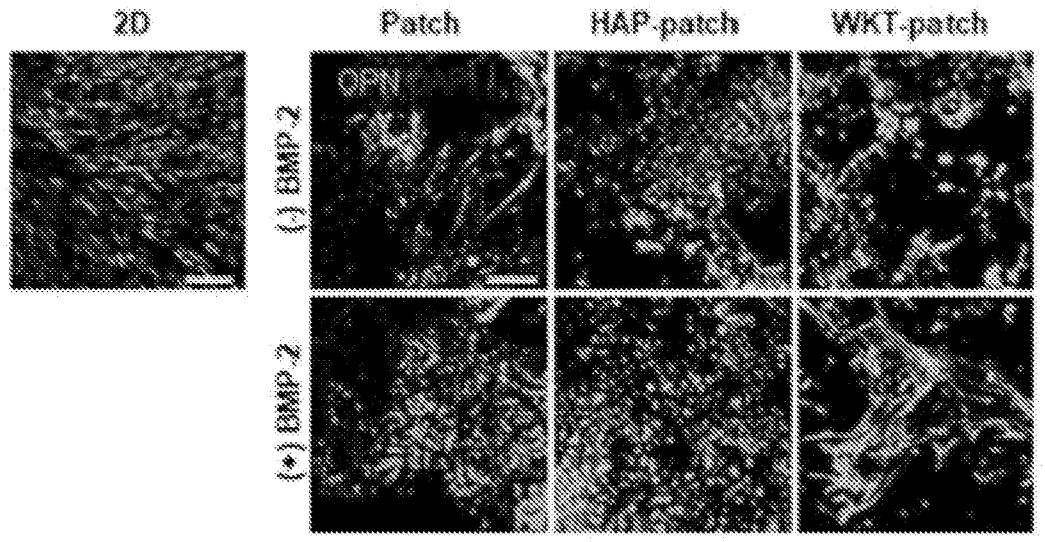
FIG. 29A shows the results of verifying bone differentiation promoting effect of the inorganic mineral particle-added HA-PG hydrogel patch loaded with BMP-2.
Figure 29B:
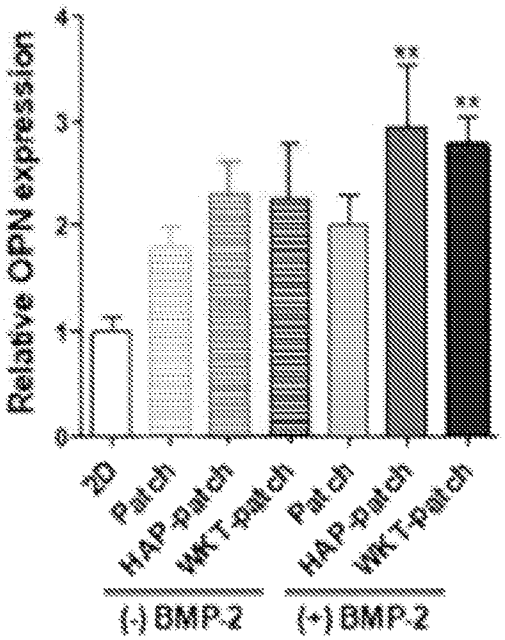
FIG. 29B shows the results of verifying bone differentiation promoting effect of the inorganic mineral particle-added HA-PG hydrogel patch loaded with BMP-2.

Meanwhile, it is confirmed by fluorescence immunostaining and qPCR analysis that the expression level of osteopontin (OPN), a bone differentiation marker, increases in the HAP- or WKT-added HA-PG hydrogel patch. In particular, it is confirmed that the expression level of the bone differentiation marker further increases in the case where BMP-2 is loaded (FIGS. 29A and 29B).

Figure 30A:
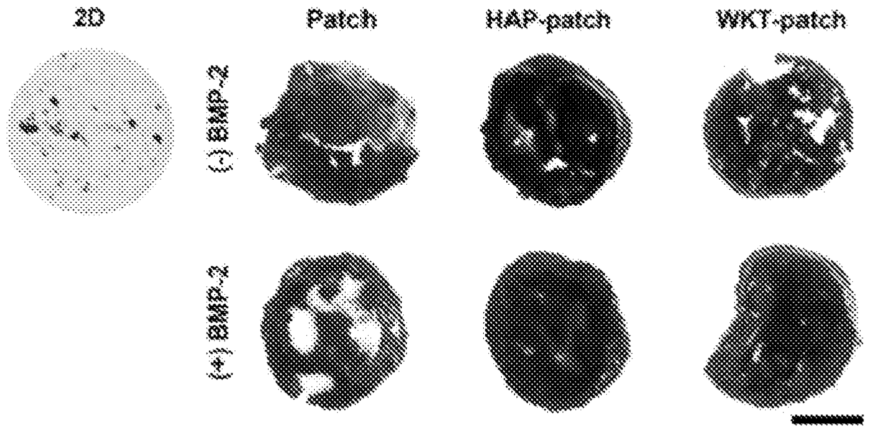
FIG. 30A shows the results of verifying bone differentiation promoting effect of the inorganic mineral particle-added HA-PG hydrogel patch loaded with BMP-2.
Figure 30B:
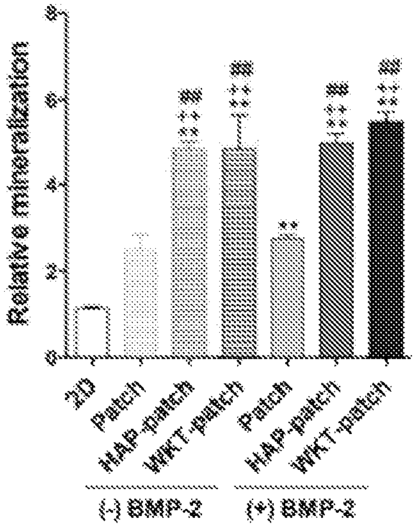
FIG. 30B shows the results of verifying bone differentiation promoting effect of the inorganic mineral particle-added HA-PG hydrogel patch loaded with BMP-2.

Meanwhile, it is confirmed by Alizarin Red S staining that the degree of calcium deposition after stem cell bone differentiation increases in the HAP- or WKT-added HA-PG hydrogel patch. In particular, it is confirmed that bone mineralization through calcium deposition is further promoted in the case where BMP-2 is loaded (FIG. 30A). Also, it is confirmed by quantitative analysis based on Alizarin Red S staining images that bone mineralization is further promoted in the HAP- or WKT-added HA-PG hydrogel patch particularly in the case where BMP-2 is loaded as compared with in 2D plate culture (2D) and the HA-PG hydrogel patch (Patch) (FIG. 30B).

Figure 31A:
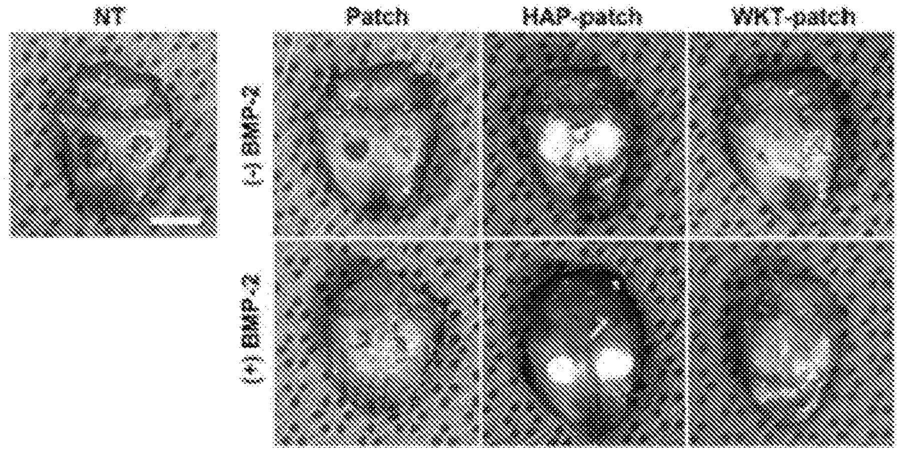
FIG. 31A shows the results of evaluating treatment efficacy of the inorganic mineral particle-added HA-PG hydrogel patch loaded with BMP-2 on a bone defect model.
Figure 31B:
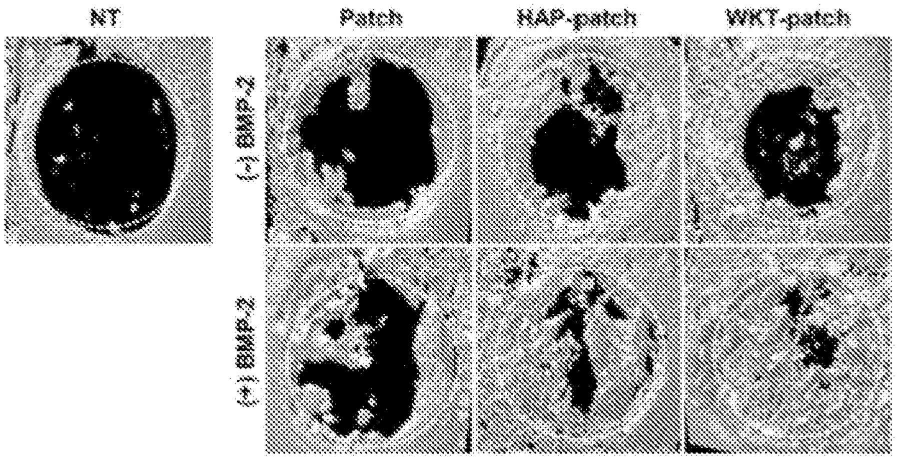
FIG. 31B shows the results of evaluating treatment efficacy of the inorganic mineral particle-added HA-PG hydrogel patch loaded with BMP-2 on a bone defect model.
Figure 31C:
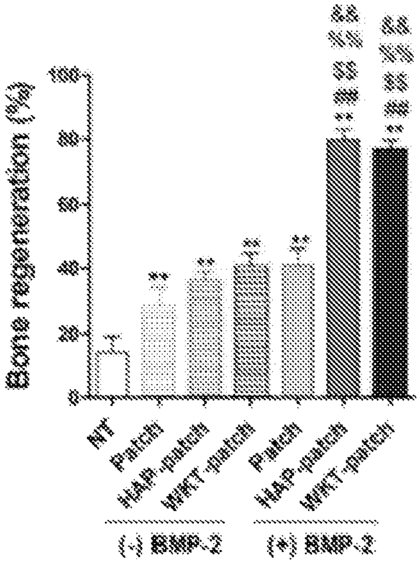
FIG. 31C shows the results of evaluating treatment efficacy of the inorganic mineral particle-added HA-PG hydrogel patch loaded with BMP-2 on a bone defect model.

(3) Evaluation of Treatment Efficacy of Inorganic Mineral Particle-Added HA-PG Hydrogel Patch Loaded with BMP-2 on Bone Defect Model The HA-PG hydrogel patch, the HAP-added HA-PG hydrogel patch, the WKT-added HA-PG hydrogel patch, the HA-PG hydrogel patch loaded with BMP-2, the HAP-added HA-PG hydrogel patch loaded with BMP-2 or the WKT-added HA-PG hydrogel patch loaded with BMP-2 was applied to a defect site and sampled 8 weeks later. Then, the patches were confirmed to be well fixed to the defect site and the degree of bone regeneration was checked with the naked eye (FIG. 31A). As a result of micro-CT taken 8 weeks later, it is confirmed that the defect size is significantly reduced when any patch is applied. In particular, it is confirmed that the defect size is more significantly reduced in the HAP- or WKT-added HA-PG hydrogel patch particularly in the case where BMP-2 is loaded (FIG. 31B). Also, it is confirmed by quantitative analysis based on micro-CT images that bone regeneration is significantly promoted in the HAP- or WKT-added HA-PG hydrogel patch loaded with BMP-2 (FIG. 31C).

Figure 32A:
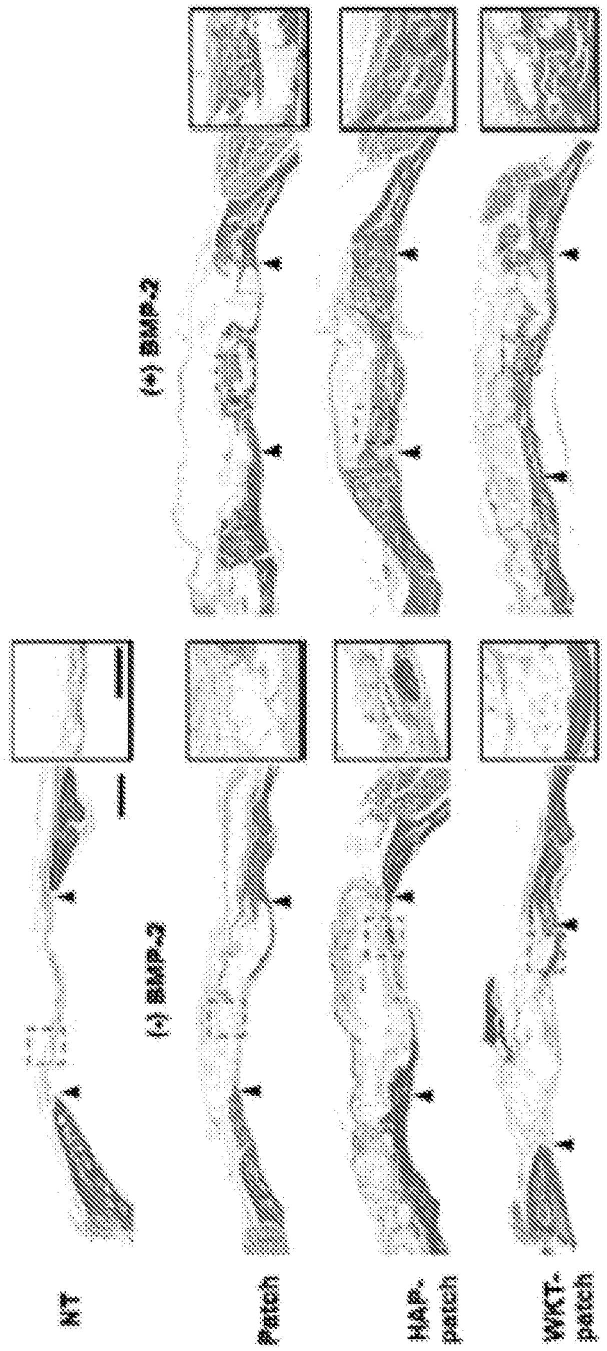
FIG. 32A shows the results of evaluating treatment efficacy of the inorganic mineral particle-added HA-PG hydrogel patch loaded with BMP-2 on a bone defect model.
Figure 32B:
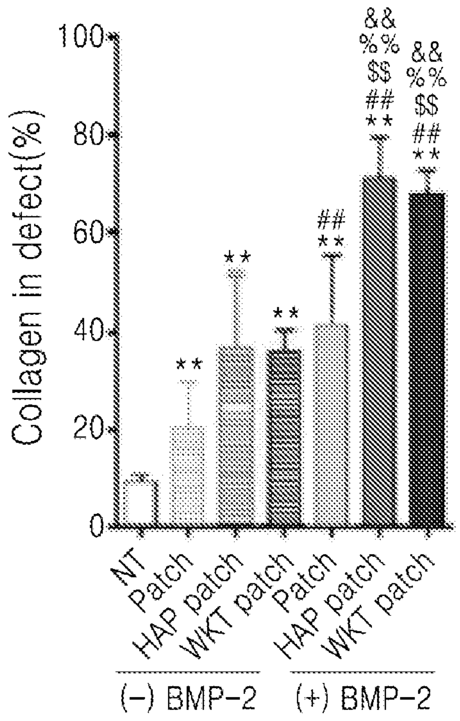
FIG. 32B shows the results of evaluating treatment efficacy of the inorganic mineral particle-added HA-PG hydrogel patch loaded with BMP-2 on a bone defect model.
Figure 32C:
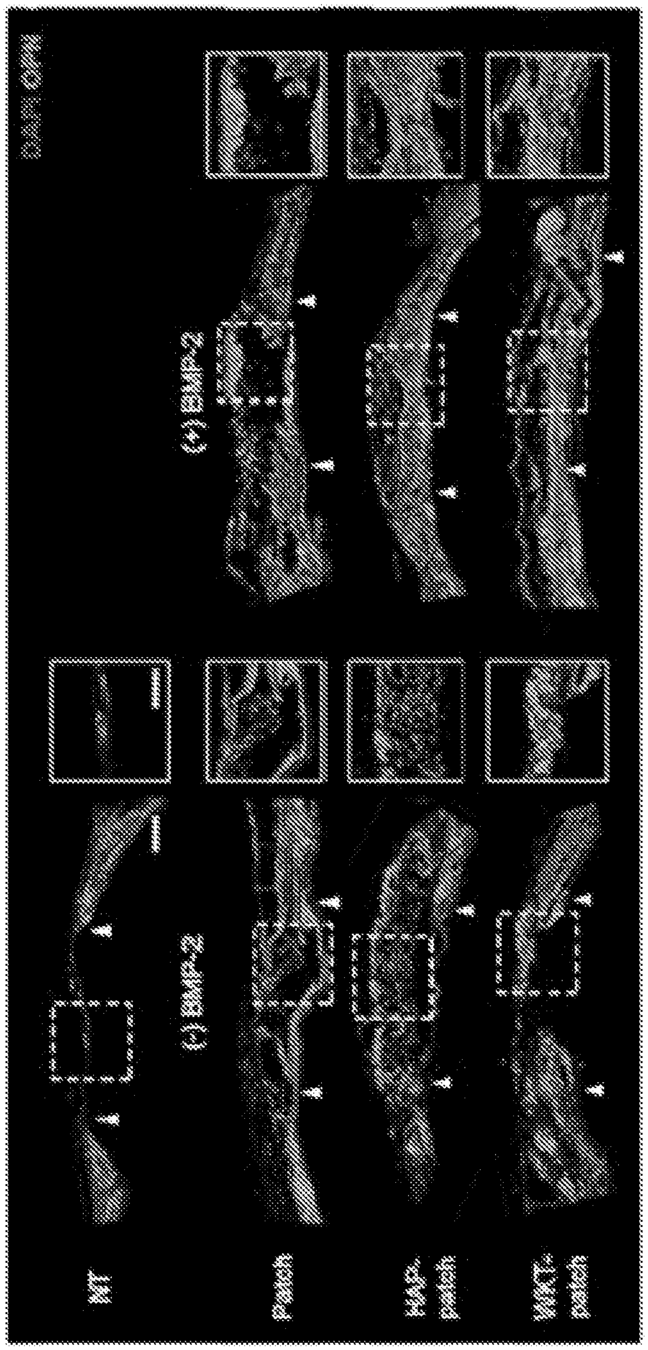
FIG. 32C shows the results of evaluating treatment efficacy of the inorganic mineral particle-added HA-PG hydrogel patch loaded with BMP-2 on a bone defect model.
Figure 32D:
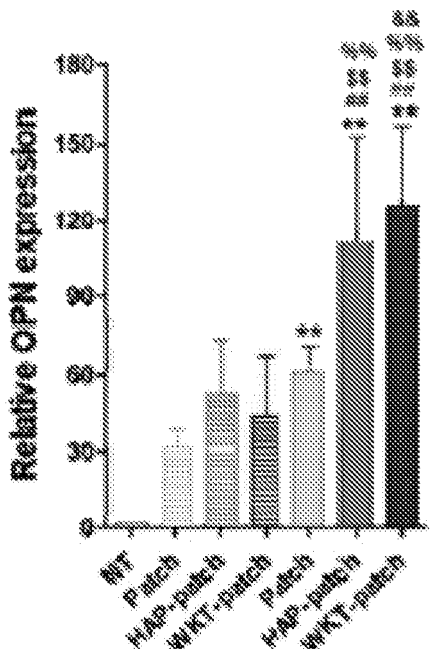
FIG. 32D shows the results of evaluating treatment efficacy of the inorganic mineral particle-added HA-PG hydrogel patch loaded with BMP-2 on a bone defect model.

Meanwhile, in order to evaluate the degree of bone regeneration at a bone defect site, Goldner's trichrome staining and image-based quantitative analysis was performed at 8 weeks after treatment, and collagen regeneration was greatly promoted in the HAP- or WKT-added HA-PG hydrogel patch loaded with BMP-2 (FIGS. 32A and 32B). Likewise, when immunostaining for the bone regeneration marker (OPN) was performed, bone regeneration was greatly promoted in the HAP- or WKT-added HA-PG hydrogel patch loaded with BMP-2 (FIGS. 32A and 32B).

Therefore, it is considered that the HA-PG hydrogel patch is well fixed to a defect site, effectively delivers inorganic ions and a drug (particularly, bone morphogenetic protein), provides a microenvironment for bone formation and thus promotes bone regeneration.

The above description of the present disclosure is provided for the purpose of illustration, and it would be understood by a person with ordinary skill in the art that various changes and modifications may be made without changing technical conception and essential features of the present disclosure. Thus, it is clear that the above-described examples are illustrative in all aspects and do not limit the present disclosure.

The invention claimed is:

1. A hydrogel patch for preventing or treating cartilage or bone diseases, comprising: a biocompatible polymer functionalized with a phenol group; a drug for treating cartilage or bone diseases loaded in the hydrogel patch; and inorganic mineral particles, wherein the biocompatible polymer is pyrogallol-functionalized hyaluronic acid with 5-hydroxydopamine (HA-PG) and the inorganic mineral particles are hydroxyapatite (HAP) or whitlockite (WKT).

2. The hydrogel patch for preventing or treating cartilage or bone diseases of claim 1, wherein the hydrogel patch has i) a thickness of from 0.05 mm to 10.0 mm, ii) a storage modulus G' of from $1\times10^3$ Pa to $1\times10^6$ Pa in a frequency range of from 0.1 Hz to 10 Hz, iii) a friction factor of from 0.2 to 0.4 as measured at a speed of 0.01 m/s under a normal force of 5 N, and iv) an adhesive strength of from 10 kPa to 20 kPa.

3. The hydrogel patch for preventing or treating cartilage or bone diseases of claim 1, wherein the inorganic mineral particles include one or more inorganic ions selected from the group consisting of calcium, magnesium and phosphorus.

4. The hydrogel patch for preventing or treating cartilage or bone diseases of claim 3, wherein the inorganic ions interact with the phenol group to form a complex compound through coordination bonding.

5. The hydrogel patch for preventing or treating cartilage or bone diseases of claim 3, wherein the inorganic ions make ionic interactions with the drug.

6. The hydrogel patch for preventing or treating cartilage or bone diseases of claim 1, wherein the drug contains:

an anti-inflammatory agent selected from the group consisting of dexamethasone, cortisone, prednisolone, hydrocortisone, triamcinolone, methylprednisolone, prednisone and betamethasone; or a bone morphogenic protein selected from the group consisting of BMP-2 (BMP-2a), BMP-3 (osteogenin), BMP-4 (BMP-2b), BMP-6 (human homologue of the murine, Vgr-1), BMP-7 (osteogenic protein-1) and BMP-9 (growth differentiation factor 2).

7. The hydrogel patch for preventing or treating cartilage or bone diseases of claim 1, wherein the cartilage disease is selected from the group consisting of inflammatory arthritis, degenerative arthritis, osteochondromatosis, distortion, bursitis, menstruation, meniscal tear, meniscus cyst, collateral ligament rupture, anterior cruciate ligament injury, posterior cruciate ligament injury, intraarticular vitreous, exfoliation osteochondritis, plica syndrome, genu varum, knock-knee and snapping knee, and the bone disease is selected from the group consisting of growth retardation, osteopenia, osteopsathyrosis, osteonecrosis, fracture, osteoporosis due to excessive bone resorption by osteoclasts, osteogenesis imperfecta, bone damage, joint damage due to trauma, osteomalacia, rickets, fibrous osteitis, aplastic bone disease, metabolic bone disease, renal osteodystrophy, periodontal disease, Paget disease and metastatic bone cancers.

* * * * *